US009206237B2

(12) United States Patent
Kimura et al.

(10) Patent No.: US 9,206,237 B2
(45) Date of Patent: Dec. 8, 2015

(54) CYSTINE KNOT PEPTIDES THAT BIND ALPHA-V-BETA-6 INTEGRIN

(71) Applicant: The Board of Trustees of the Leland Stanford Junior University, Palo Alto, CA (US)

(72) Inventors: Richard H. Kimura, Menlo Park, CA (US); Sanjiv S. Gambhir, Stanford, CA (US); Benjamin J. Hackel, Edina, MN (US); Robert Teed, Menlo Park, CA (US); Bin Shen, Mountain View, CA (US); Frederick T Chin, Sunnyvale, CA (US); Zhen Cheng, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/283,830

(22) Filed: May 21, 2014

(65) Prior Publication Data

US 2014/0271469 A1 Sep. 18, 2014

Related U.S. Application Data

(63) Continuation-in-part of application No. PCT/US2012/066148, filed on Nov. 20, 2012.

(60) Provisional application No. 61/562,708, filed on Nov. 22, 2011.

(51) Int. Cl.
*C07K 14/00* (2006.01)
*A61K 51/08* (2006.01)
*G01N 33/574* (2006.01)
*G01N 33/68* (2006.01)

(52) U.S. Cl.
CPC ............ *C07K 14/001* (2013.01); *A61K 51/088* (2013.01); *G01N 33/574* (2013.01); *G01N 33/57492* (2013.01); *G01N 33/6863* (2013.01); *G01N 2333/70546* (2013.01)

(58) Field of Classification Search
None
See application file for complete search history.

(56) References Cited

U.S. PATENT DOCUMENTS

| 6,020,460 | A | 2/2000 | Pierschbacher et al. |
| 8,536,301 | B2 | 9/2013 | Cochran et al. |
| 8,778,888 | B2 | 7/2014 | Cochran et al. |
| 2007/0128203 | A1 | 6/2007 | Giles-Komar et al. |
| 2009/0123370 | A1 | 5/2009 | Howard et al. |
| 2009/0130692 | A1 | 5/2009 | Kolmar et al. |
| 2009/0257952 | A1 | 10/2009 | Cochran et al. |
| 2010/0267610 | A1 | 10/2010 | Blind et al. |
| 2011/0136740 | A1 | 6/2011 | Cochran et al. |
| 2014/0073518 | A1 | 3/2014 | Cochran et al. |

FOREIGN PATENT DOCUMENTS

| WO | 2008045252 A2 | 4/2008 |
| WO | 2008098796 A1 | 8/2008 |
| WO | 2014063012 A1 | 4/2014 |

OTHER PUBLICATIONS

Camarero, J.A., "Developing New Tools for the in vivo Generation/Screening of Cyclic Peptide Libraries. A New Combinatorial Approach for the Detection of Bacterial Toxin Inhibitors." LLNL Report, UCRL-TR-227590, 2007, 11 pp.
Cantor, J., et al., "Biosynthesis of the Cyclotide MCo TI-II using an Engineered Intein," LLNL Report, UCRL-TR-223848, 2006, 12 pp.
Chen, S., et al., "Synthesis of Diverse Tracers on Ewod Microdevice for Positron Emission Tomography (PET)," Solid-State Sensors, Actuators, and Microsystems Workshop, Hilton Head Island, South Carolina, Jun. 3-7, 2012, pp. 189-191.
Christmann, Andreas, et al., "The cystine knot of a squash-type protease inhibitor as a structural scaffold for *Escherichia coli* cell surface display of conformationally constrained peptides," Protein Engineering, 1999, vol. 12, No. 9, pp. 797-806.
Clark, Richard J., et al., "Structural plasticity of the cyclic-cystine-knot framework: implications for biological activity and drug design," Biochem. J., 2006, vol. 394, pp. 85-93.
Copie, Valerie, et al, "Solution Structure and Dynamics of Linked Cell Attachment Modules of Mouse Fibronectin Containing the RGD and Synergy Regions: Comparison with the Human Fibronectin Crystal Structure," J. Mol. Biol. 1998, vol. 277, pp. 663-682.
DiCara, Danielle, et al., "Structure-Function Analysis of Arg-Gly-Asp Helix Motifs in αvβ6 Integrin Ligands," The Journal of Biological Chemistry, 2007, vol. 28, No. 13, pp. 9657-9665.
Daly, Norelle L., et al., "Disulfide Folding Pathways of Cystine Knot Proteins," The Journal of Biological Chemistry, 2003, vol. 278, No. 8, pp. 6314-6322.

(Continued)

*Primary Examiner* — Karlheinz R Skowronek
*Assistant Examiner* — Lianko Garyu
(74) *Attorney, Agent, or Firm* — David J. Aston; Bozicevic, Field & Francis LLP

(57) ABSTRACT

Disclosed are peptides comprising a molecular scaffold portion and a loop portion that binds to integrin $\alpha_v\beta_6$. This integrin is expressed on pancreatic tumors, making the peptides useful as imaging agents, among other uses. The peptides showed single-digit nanomolar dissociation constants similar to antibodies used clinically for imaging and therapy. The peptides rapidly accumulated in $\alpha_v\beta_6$-positive tumors, which led to excellent tumor-to-normal contrast. The peptides are specific for the targeted integrin $\alpha_v\beta_6$ receptors expressed on orthotopic pancreatic tumors and various xenografts used. Additionally, pharmacokinetic-stabilization strategies endowed knots with rapid renal clearance, which significantly reduced off-target dosing.

22 Claims, 13 Drawing Sheets

(56) References Cited

OTHER PUBLICATIONS

Gelly, Jean-Christophe, et al., "The KNOTTIN website and database: a new information system dedicated to the knottin scaffold," Nucleic Acids Research, 2004, vol. 32, Database Issue, Oxford University Press, pp. D156-D159.

Hautanen, Aarno, et al., "Effects of Modifications of the RGD Sequence and Its Context on Recognition by the Fibronectin Receptor," The Journal of Biological Chemistry, 1989, vol. 264, No. 3, pp. 1437-1442.

Heitz, Annie, et al., "Knottin cyclization: impact on structure and dynamics," BMC Structural Biology, 2008, 8:54, 19 pp.

Hwang, Jae-Sam, et al., Isolation and Characterization of Psacotheasin, a Novel Knottin-Type Antimicrobial Peptide, from Psacothea hilaris, J. Microbiol. Biotechnol., 2010, 20:4, pp. 708-711.

Kowalska, et al., Uniprot Accession No. P83397, Aug. 10, 2010 [online]. [Retrieved on May 16, 2013]. Retrieved from the Internet: <URL: http://www.uniprot.org/uniprot/P83397.txt?version=48>, 1 p.

Kraft, Sabine, et al., "Definition of an Unexpected Ligand Recognition Motif for αvβ6 Integrin," The Journal of Biological Chemistry, 1999, vol. 274, No. 4, pp. 1979-1985.

Ling, et al., Uniprot Accession No. P35628, Aug. 10, 2010 [online]. [Retrieved on May 16, 2013]. Retrieved from the Internet: <URL: http://www.uniprot.org/uniprot/P35628.txt?version=53>, 1 p.

Skerra, Arne, "Engineered protein scaffolds for molecular recognition," J. Mol. Recognit., 2000, vol. 13, pp. 167-187.

Smith, Geoffrey P., et al., "Small Binding Proteins Selected from a Combinatorial Repertoire of Knottins Displayed on Phage," J. Mol. Biol., 1998, vol. 277, pp. 317-332.

ISR and Written Opinion, Int'l. Appl. No. PCT/US2012/66148, 2013, 9 pp.

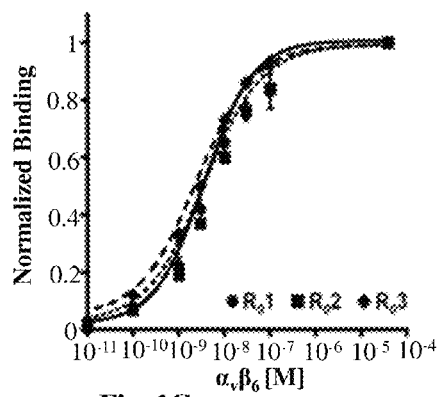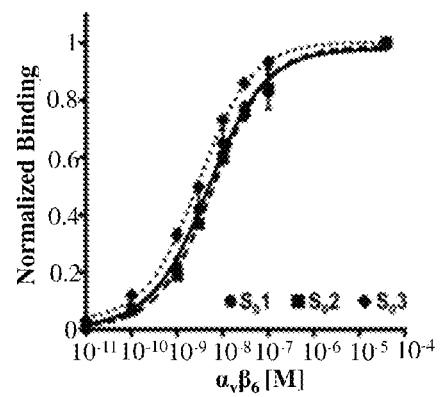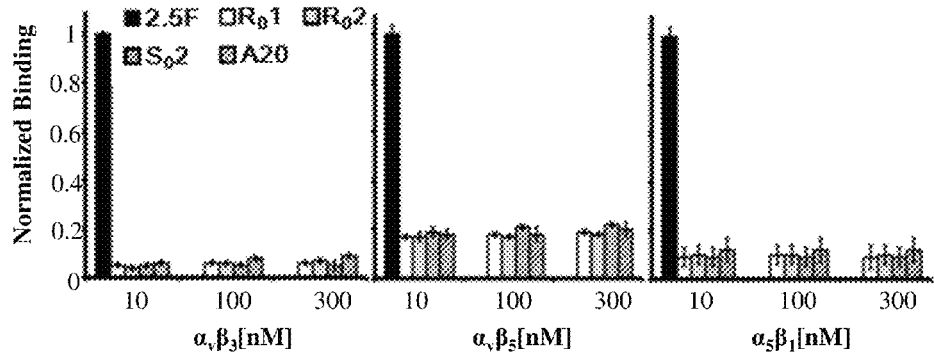
Figure 1A, 1B, and 1C

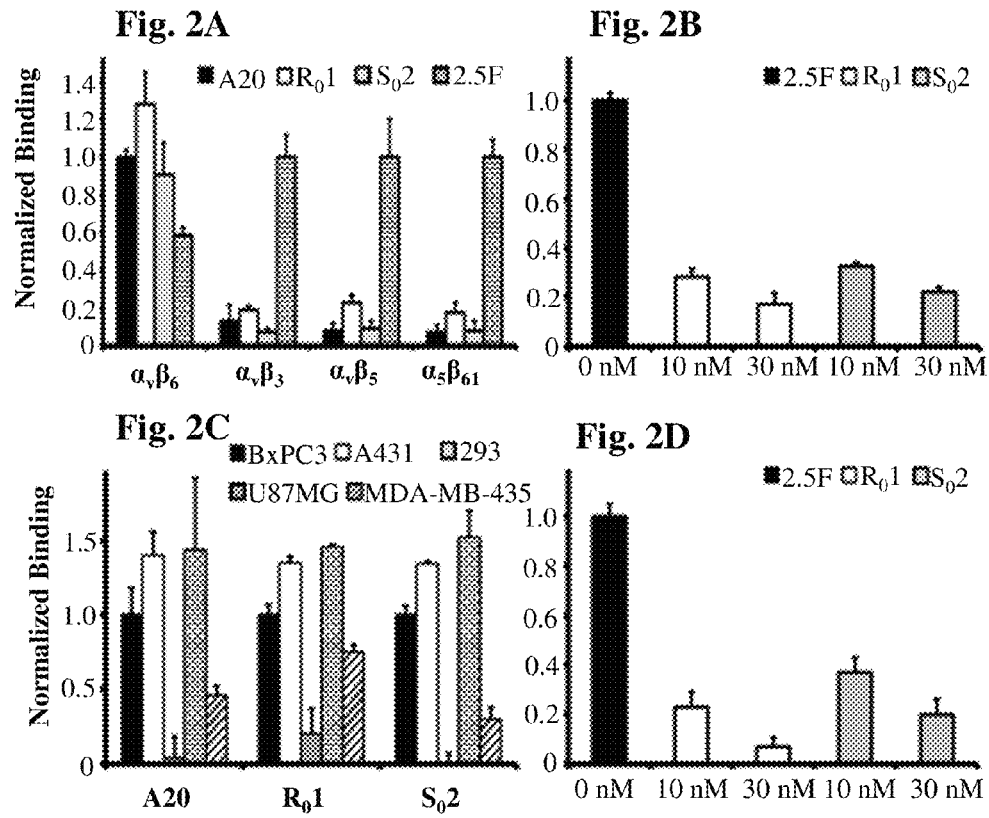
Figure 2A, 2B, 2C, and 2D

Fig. 3A
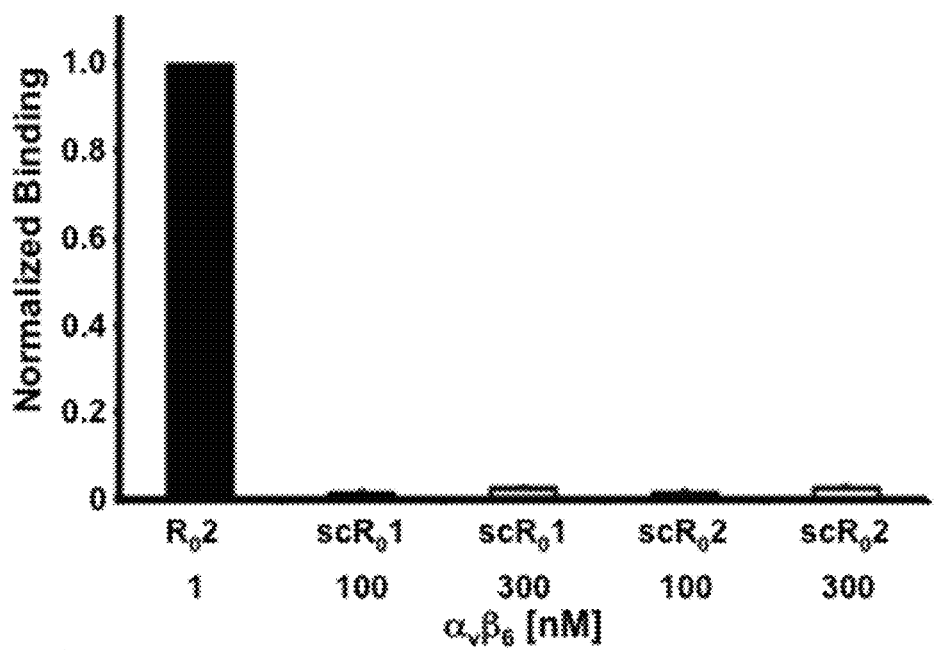
Fig. 3B
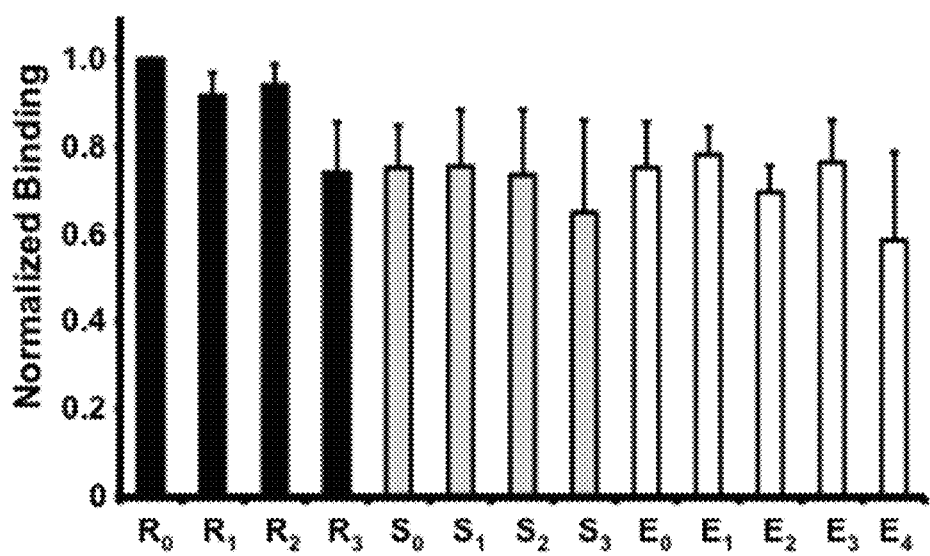
Figure 3A and 3B

SEQUENCE LISTING

<160> NUMBER OF SEQ ID NOS: 65

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 1

Arg Thr Asp Leu Asp Ser Leu Arg Thr Tyr Thr Leu
1               5                   10

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Cys Ile Leu Asn Met Arg Thr Asp Leu Gly Thr Leu Leu Phe Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Cys Arg Ser Leu Ala Arg Thr Asp Leu Asp His Leu Arg Gly Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Cys Arg Ser Leu Ala Arg Thr Asp Leu Asp His Leu Arg Gly Arg
1               5                   10                  15

Cys Glu Glu Asp Ser Asp Cys Leu Ala Glu Cys Ile Cys Glu Glu Asn
            20                  25                  30

Gly Phe Cys Gly
        35

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Cys Arg Ser Leu Ala Arg Thr Asp Leu Asp His Leu Arg Asp Arg
```

```
1               5                  10                 15
Cys Ser Ser Asp Ser Asp Cys Leu Ala Glu Cys Ile Cys Leu Glu Asn
            20                  25                 30
Gly Phe Cys Gly
        35
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid

<400> SEQUENCE: 6

```
Arg Thr Asp Leu Xaa Xaa Leu
1               5
```

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Arg Ser Leu Ala Arg Thr Asp Leu Asp His Leu Arg Gly Arg
1               5                  10
```

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Ile or Arg
<220> FEATURE:
<221> NAME/KEY: MOD_RES
<222> LOCATION: (4)..(4)
<223> OTHER INFORMATION: Leu or Ser
<220> FEATURE:
<221> NAME/KEY: MOD_RES
<222> LOCATION: (5)..(5)
<223> OTHER INFORMATION: Asn or Leu
<220> FEATURE:
<221> NAME/KEY: MOD_RES
<222> LOCATION: (6)..(6)
<223> OTHER INFORMATION: Met, Ala, Arg, Gly or Trp
<220> FEATURE:
<221> NAME/KEY: MOD_RES
<222> LOCATION: (11)..(11)
<223> OTHER INFORMATION: Gly or Asp
<220> FEATURE:
<221> NAME/KEY: MOD_RES
<222> LOCATION: (12)..(12)
<223> OTHER INFORMATION: Thr or His
<220> FEATURE:
<221> NAME/KEY: MOD_RES
<222> LOCATION: (14)..(14)
<223> OTHER INFORMATION: Leu or Arg
<220> FEATURE:
<221> NAME/KEY: MOD_RES
<222> LOCATION: (15)..(15)

```
<223> OTHER INFORMATION: Phe, Asp or Gly
<220> FEATURE:
<221> NAME/KEY: MOD_RES
<222> LOCATION: (18)..(19)
<223> OTHER INFORMATION: Arg, Glu or Ser
<220> FEATURE:
<221> NAME/KEY: MOD_RES
<222> LOCATION: (24)..(24)
<223> OTHER INFORMATION: Pro or Leu
<220> FEATURE:
<221> NAME/KEY: MOD_RES
<222> LOCATION: (25)..(25)
<223> OTHER INFORMATION: Gly or Ala
<220> FEATURE:
<221> NAME/KEY: MOD_RES
<222> LOCATION: (26)..(26)
<223> OTHER INFORMATION: Ala or Glu
<220> FEATURE:
<221> NAME/KEY: MOD_RES
<222> LOCATION: (30)..(30)
<223> OTHER INFORMATION: Arg, Glu or Leu
<220> FEATURE:
<221> NAME/KEY: MOD_RES
<222> LOCATION: (31)..(31)
<223> OTHER INFORMATION: Gly or Glu
<220> FEATURE:
<221> NAME/KEY: MOD_RES
<222> LOCATION: (34)..(34)
<223> OTHER INFORMATION: Tyr or Phe

<400> SEQUENCE: 8

Gly Cys Xaa Xaa Xaa Xaa Arg Thr Asp Leu Xaa Xaa Leu Xaa Xaa Arg
1               5                   10                  15

Cys Xaa Xaa Asp Ser Asp Cys Xaa Xaa Xaa Cys Ile Cys Xaa Xaa Asn
            20                  25                  30

Gly Xaa Cys Gly
        35

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid

<400> SEQUENCE: 9

Arg Asp Thr Leu Xaa Xaa Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(13)
<223> OTHER INFORMATION: Any amino acid

<400> SEQUENCE: 11

Xaa Xaa Xaa Arg Thr Asp Leu Xaa Xaa Leu Xaa Xaa Xaa
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid

<400> SEQUENCE: 12

Xaa Xaa Xaa Xaa Arg Thr Asp Leu Xaa Xaa Leu Xaa Xaa Xaa
1               5                   10

<210> SEQ ID NO 13
<211> LENGTH: 33
<212> TYPE: PRT
<213> ORGANISM: Momordica cochinchinensis

<400> SEQUENCE: 13

Val Cys Pro Lys Ile Leu Lys Lys Cys Arg Arg Asp Ser Asp Cys Pro
1               5                   10                  15

Gly Ala Cys Ile Cys Arg Gly Asn Gly Tyr Cys Gly Ser Gly Ser Asp
            20                  25                  30

Gly

<210> SEQ ID NO 14
<211> LENGTH: 33
<212> TYPE: PRT
<213> ORGANISM: Momordica cochinchinensis

<400> SEQUENCE: 14

Val Cys Pro Lys Ile Leu Gln Arg Cys Arg Arg Asp Ser Asp Cys Pro
1               5                   10                  15

Gly Ala Cys Ile Cys Arg Gly Asn Gly Tyr Cys Gly Ser Gly Ser Asp
            20                  25                  30

Gly
```

```
<210> SEQ ID NO 15
<211> LENGTH: 30
<212> TYPE: PRT
<213> ORGANISM: Momordica charantia

<400> SEQUENCE: 15

Glu Arg Arg Cys Pro Arg Ile Leu Lys Gln Cys Lys Arg Asp Ser Asp
1               5                   10                  15

Cys Pro Gly Glu Cys Ile Cys Met Ala His Gly Phe Cys Gly
            20                  25                  30

<210> SEQ ID NO 16
<211> LENGTH: 29
<212> TYPE: PRT
<213> ORGANISM: Bryonia dioica

<400> SEQUENCE: 16

Arg Gly Cys Pro Arg Ile Leu Met Arg Cys Lys Arg Asp Ser Asp Cys
1               5                   10                  15

Leu Ala Gly Cys Val Cys Gln Lys Asn Gly Tyr Cys Gly
            20                  25

<210> SEQ ID NO 17
<211> LENGTH: 29
<212> TYPE: PRT
<213> ORGANISM: Momordica repens

<400> SEQUENCE: 17

Gly Ile Cys Pro Arg Ile Leu Met Glu Cys Lys Arg Asp Ser Asp Cys
1               5                   10                  15

Leu Ala Gln Cys Val Cys Lys Arg Gln Gly Tyr Cys Gly
            20                  25

<210> SEQ ID NO 18
<211> LENGTH: 28
<212> TYPE: PRT
<213> ORGANISM: Momordica charantia

<400> SEQUENCE: 18

Arg Ile Cys Pro Arg Ile Trp Met Glu Cys Lys Arg Asp Ser Asp Cys
1               5                   10                  15

Met Ala Gln Cys Ile Cys Val Asp Gly His Cys Gly
            20                  25

<210> SEQ ID NO 19
<211> LENGTH: 32
<212> TYPE: PRT
<213> ORGANISM: Cucurbita maxima

<400> SEQUENCE: 19

His Glu Glu Arg Val Cys Pro Arg Ile Leu Met Lys Cys Lys Lys Asp
1               5                   10                  15

Ser Asp Cys Leu Ala Glu Cys Val Cys Leu Glu His Gly Tyr Cys Gly
            20                  25                  30

<210> SEQ ID NO 20
<211> LENGTH: 29
<212> TYPE: PRT
<213> ORGANISM: Cucumis melo

<400> SEQUENCE: 20

Arg Val Cys Pro Arg Ile Leu Met Glu Cys Lys Lys Asp Ser Asp Cys
1               5                   10                  15
```

```
Leu Ala Glu Cys Val Cys Leu Glu His Gly Tyr Cys Gly
        20                  25

<210> SEQ ID NO 21
<211> LENGTH: 32
<212> TYPE: PRT
<213> ORGANISM: Cucumis melo

<400> SEQUENCE: 21

His Glu Glu Arg Gly Cys Pro Arg Ile Leu Met Lys Cys Lys Lys Asp
1               5                   10                  15

Ser Asp Cys Leu Ala Glu Cys Val Cys Leu Glu His Gly Tyr Cys Gly
            20                  25                  30

<210> SEQ ID NO 22
<211> LENGTH: 32
<212> TYPE: PRT
<213> ORGANISM: Cucurbita pepo

<400> SEQUENCE: 22

His Glu Glu Arg Val Cys Pro Arg Ile Leu Met Glu Cys Lys Lys Asp
1               5                   10                  15

Ser Asp Cys Leu Ala Glu Cys Ile Cys Leu Glu His Gly Tyr Cys Gly
            20                  25                  30

<210> SEQ ID NO 23
<211> LENGTH: 29
<212> TYPE: PRT
<213> ORGANISM: Ecballium elaterium

<400> SEQUENCE: 23

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly Ser
            20                  25

<210> SEQ ID NO 24
<211> LENGTH: 30
<212> TYPE: PRT
<213> ORGANISM: Momordica charantia

<400> SEQUENCE: 24

Glu Arg Gly Cys Pro Arg Ile Leu Lys Gln Cys Lys Gln Asp Ser Asp
1               5                   10                  15

Cys Pro Gly Glu Cys Ile Cys Met Ala His Gly Phe Cys Gly
            20                  25                  30

<210> SEQ ID NO 25
<211> LENGTH: 30
<212> TYPE: PRT
<213> ORGANISM: Cucumis melo

<400> SEQUENCE: 25

Gln Arg Met Cys Pro Lys Ile Leu Met Lys Cys Lys Gln Asp Ser Asp
1               5                   10                  15

Cys Leu Leu Asp Cys Val Cys Leu Lys Glu Gly Phe Cys Gly
            20                  25                  30

<210> SEQ ID NO 26
<211> LENGTH: 28
<212> TYPE: PRT
<213> ORGANISM: Cucumis melo
```

<400> SEQUENCE: 26

Met Cys Pro Lys Ile Leu Met Lys Cys Lys Gln Asp Ser Asp Cys Leu
1               5                   10                  15

Leu Asp Cys Val Cys Leu Lys Glu Gly Phe Cys Gly
            20                  25

<210> SEQ ID NO 27
<211> LENGTH: 30
<212> TYPE: PRT
<213> ORGANISM: Cucumis sativus

<400> SEQUENCE: 27

Met Met Cys Pro Arg Ile Leu Met Lys Cys Lys His Asp Ser Asp Cys
1               5                   10                  15

Leu Pro Gly Cys Val Cys Leu Glu His Ile Glu Tyr Cys Gly
            20                  25                  30

<210> SEQ ID NO 28
<211> LENGTH: 31
<212> TYPE: PRT
<213> ORGANISM: Cucumis sativus

<400> SEQUENCE: 28

Met Val Cys Pro Arg Ile Leu Met Lys Cys Lys His Asp Ser Asp Cys
1               5                   10                  15

Leu Leu Asp Cys Val Cys Leu Glu Asp Ile Gly Tyr Cys Gly Val
            20                  25                  30

<210> SEQ ID NO 29
<211> LENGTH: 28
<212> TYPE: PRT
<213> ORGANISM: Luffa cylindrica

<400> SEQUENCE: 29

Ile Cys Pro Arg Ile Leu Met Pro Cys Ser Ser Asp Ser Asp Cys Leu
1               5                   10                  15

Ala Glu Cys Ile Cys Leu Glu Asn Gly Phe Cys Gly
            20                  25

<210> SEQ ID NO 30
<211> LENGTH: 29
<212> TYPE: PRT
<213> ORGANISM: Luffa cylindrica

<400> SEQUENCE: 30

Arg Ile Cys Pro Arg Ile Leu Met Glu Cys Ser Ser Asp Ser Asp Cys
1               5                   10                  15

Leu Ala Glu Cys Ile Cys Leu Glu Asn Gly Phe Cys Gly
            20                  25

<210> SEQ ID NO 31
<211> LENGTH: 29
<212> TYPE: PRT
<213> ORGANISM: Luffa cylindrica

<400> SEQUENCE: 31

Arg Ile Cys Pro Arg Ile Leu Met Glu Cys Ser Ser Asp Ser Asp Cys
1               5                   10                  15

Leu Ala Glu Cys Ile Cys Leu Glu Gln Gly Phe Cys Gly
            20                  25

```
<210> SEQ ID NO 32
<211> LENGTH: 29
<212> TYPE: PRT
<213> ORGANISM: Luffa cylindrica

<400> SEQUENCE: 32

Arg Ile Cys Pro Arg Ile Leu Met Glu Cys Ser Ser Asp Ser Asp Cys
1               5                   10                  15

Leu Ala Glu Cys Ile Cys Leu Glu Gln Gly Phe Cys Gly
            20                  25

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Cys Pro Lys Ile Leu Lys Lys Cys Arg Arg Asp Ser Asp Cys Pro
1               5                   10                  15

Gly Ala Cys Ile Cys Arg Gly Asn Gly Tyr Cys Gly
            20                  25

<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Cys His Pro Arg Thr Asp Leu Ala Ser Leu Ala Lys Arg Cys Arg
1               5                   10                  15

Arg Asp Ser Asp Cys Pro Gly Ala Cys Ile Cys Arg Gly Asn Gly Tyr
            20                  25                  30

Cys Gly

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Cys Gly His Pro Arg Thr Asp Leu Ala Ser Leu Ala Lys Arg Cys
1               5                   10                  15

Arg Arg Asp Ser Asp Cys Pro Gly Ala Cys Ile Cys Arg Gly Asn Gly
            20                  25                  30

Tyr Cys Gly
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 36

Gly Cys Gly Gly His Pro Arg Thr Asp Leu Ala Ser Leu Ala Lys Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Cys His Pro Arg Thr Asp Leu Ala Ser Leu Ala Lys Arg Gly Cys
1               5                   10                  15

Arg Arg Asp Ser Asp Cys Pro Gly Ala Cys Ile Cys Arg Gly Asn Gly
            20                  25                  30

Tyr Cys Gly
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Cys Gly His Pro Arg Thr Asp Leu Ala Ser Leu Ala Lys Arg Gly
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Cys Gly Gly His Pro Arg Thr Asp Leu Ala Ser Leu Ala Lys Arg
1               5                   10                  15

Gly Cys Arg Arg Asp Ser Asp Cys Pro Gly Ala Cys Ile Cys Arg Gly
            20                  25                  30

Asn Gly Tyr Cys Gly
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 40

Gly Cys His Pro Arg Thr Asp Leu Ala Ser Leu Ala Lys Arg Gly Gly
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Cys Gly His Pro Arg Thr Asp Leu Ala Ser Leu Ala Lys Arg Gly
1               5                   10                  15

Gly Cys Arg Arg Asp Ser Asp Cys Pro Gly Ala Cys Ile Cys Arg Gly
            20                  25                  30

Asn Gly Tyr Cys Gly
        35

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Cys Gly Gly His Pro Arg Thr Asp Leu Ala Ser Leu Ala Lys Arg
1               5                   10                  15

Gly Gly Cys Arg Arg Asp Ser Asp Cys Pro Gly Ala Cys Ile Cys Arg
            20                  25                  30

Gly Asn Gly Tyr Cys Gly
        35

<210> SEQ ID NO 43
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 43

Gly Cys Xaa Xaa Xaa Arg Thr Asp Leu Xaa Xaa Leu Xaa Xaa Xaa Cys
1               5                   10                  15

Arg Arg Asp Ser Asp Cys Pro Gly Ala Cys Ile Cys Arg Gly Asn Gly
```

Tyr Cys Gly
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 44

Gly Cys Xaa Xaa Xaa Xaa Arg Thr Asp Leu Xaa Xaa Leu Xaa Xaa Xaa
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 45

Gly Cys Arg Xaa Xaa Xaa Arg Thr Asp Leu Xaa Xaa Leu Arg Xaa Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 46

Gly Cys Arg Xaa Arg Xaa Arg Thr Asp Leu Xaa Xaa Leu Arg Xaa Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Cys Arg Leu Val Phe Arg Thr Asp Leu Asp His Leu Arg Gly Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Cys Arg Ser Leu Ala Arg Thr Asp Leu Asp His Leu Arg Gly Arg
1               5                   10                  15

Cys Arg Arg Asp Arg Asp Cys Pro Gly Ala Cys Ile Cys Arg Gly Asn
            20                  25                  30

Gly Tyr Cys Gly
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Cys Arg Ser Leu Ala Arg Thr Asp Leu Asp His Leu Arg Gly Arg
1               5                   10                  15
```

Cys Arg Arg Asp Ser Asp Cys Arg Gly Ala Cys Ile Cys Arg Gly Asn
            20                  25                  30

Gly Tyr Cys Gly
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Cys Arg Ser Leu Ala Arg Thr Asp Leu Asp His Leu Arg Gly Arg
1               5                   10                  15

Cys Arg Arg Asp Arg Asp Cys Arg Gly Ala Cys Ile Cys Arg Gly Asn
            20                  25                  30

Gly Tyr Cys Gly
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Cys Arg Ser Leu Ala Arg Thr Asp Leu Asp His Leu Arg Gly Arg
1               5                   10                  15

Cys Arg Arg Asp Ser Asp Cys Pro Gly Ala Cys Ile Cys Glu Gly Asn
            20                  25                  30

Gly Tyr Cys Gly
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Cys Arg Ser Leu Ala Arg Thr Asp Leu Asp His Leu Arg Gly Arg
1               5                   10                  15

Cys Arg Glu Asp Ser Asp Cys Pro Gly Ala Cys Ile Cys Arg Gly Asn
            20                  25                  30

Gly Tyr Cys Gly
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Cys Arg Ser Leu Ala Arg Thr Asp Leu Asp His Leu Arg Gly Arg

```
                 1               5                  10                 15
Cys Glu Arg Asp Ser Asp Cys Pro Gly Ala Cys Ile Cys Arg Gly Asn
                        20                 25                 30

Gly Tyr Cys Gly
            35

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Cys Arg Ser Leu Ala Arg Thr Asp Leu Asp His Leu Arg Gly Arg
1               5                  10                 15

Cys Glu Glu Asp Ser Asp Cys Pro Gly Ala Cys Ile Cys Glu Gly Asn
                        20                 25                 30

Gly Tyr Cys Gly
            35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Cys Arg Ser Leu Ala Arg Thr Asp Leu Asp His Leu Arg Gly Arg
1               5                  10                 15

Cys Glu Glu Asp Ser Asp Cys Leu Ala Glu Cys Ile Cys Glu Glu Asn
                        20                 25                 30

Gly Phe Cys Gly
            35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Cys Arg Ser Leu Ala Arg Thr Asp Leu Asp His Leu Arg Gly Arg
1               5                  10                 15

Cys Ser Ser Asp Ser Asp Cys Leu Ala Glu Cys Ile Cys Leu Glu Asn
                        20                 25                 30

Gly Phe Cys Gly
            35

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57
```

```
Gly Cys Arg Ser Leu Ala Arg Thr Asp Leu Asp His Leu Arg Gly Arg
1               5                   10                  15

Cys Ser Ser Asp Ser Asp Cys Ser Ala Glu Cys Ile Cys Leu Glu Asn
            20                  25                  30

Gly Phe Cys Gly
        35

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Cys Arg Ser Leu Ala Arg Thr Asp Leu Asp His Leu Arg Gly Arg
1               5                   10                  15

Cys Ser Ser Asp Ser Asp Cys Leu Ala Glu Cys Ile Cys Ser Glu Asn
            20                  25                  30

Gly Phe Cys Gly
        35

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Cys Arg Ser Leu Ala Arg Thr Asp Leu Asp His Leu Arg Gly Arg
1               5                   10                  15

Cys Ser Ser Asp Ser Asp Cys Ser Ala Glu Cys Ile Cys Ser Glu Asn
            20                  25                  30

Gly Phe Cys Gly
        35

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ile Leu Asn Arg Arg Thr Asp Leu Gly Thr Leu Leu Phe Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ile Leu Asn Gly Arg Thr Asp Leu Gly Thr Leu Leu Phe Arg
1               5                   10

<210> SEQ ID NO 62
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ile Leu Asn Trp Arg Thr Asp Leu Gly Thr Leu Leu Phe Arg
1               5                   10

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Cys Ile Leu Asn Arg Arg Thr Asp Leu Gly Thr Leu Leu Phe Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Cys Ile Leu Asn Gly Arg Thr Asp Leu Gly Thr Leu Leu Phe Arg
1               5                   10                  15

Cys Arg Arg Asp Ser Asp Cys Pro Gly Ala Cys Ile Cys Arg Gly Asn
            20                  25                  30

Gly Tyr Cys Gly
        35

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Cys Ile Leu Asn Trp Arg Thr Asp Leu Gly Thr Leu Leu Phe Arg
1               5                   10                  15

Cys Arg Arg Asp Ser Asp Cys Pro Gly Ala Cys Ile Cys Arg Gly Asn
            20                  25                  30

Gly Tyr Cys Gly
        35
```

CYSTINE KNOT PEPTIDES THAT BIND ALPHA-V-BETA-6 INTEGRIN

CROSS-REFERENCE TO RELATED APPLICATIONS

This application is a continuation-in-part of and claims priority to Ser. No. US PCT/US2012/066148, filed 20 Nov. 2012, which in turn claims priority to Provisional Patent Application No. 61/562,708, filed 22 Nov. 2011, both of which are hereby incorporated by reference in their entirety.

STATEMENT OF GOVERNMENTAL SUPPORT

This invention was made with Government support under contract P50CA114747 awarded by the National Institutes of Health. The Government has certain rights in this invention.

REFERENCE TO SEQUENCE LISTING, COMPUTER PROGRAM, OR COMPACT DISK

In accordance with "Legal Framework for EFS-Web," (2006 Apr. 11) submit herewith is a sequence listing as an ASCII text file. The text file will serve as both the paper copy required by 37 CFR 1.821(c) and the computer readable form (CRF) required by 37 CFR 1.821(e). The date of creation of the file was May 20, 2014, and the size of the ASCII text file in bytes is 27,801. Applicant incorporates the contents of the sequence listing by reference in its entirety.

BACKGROUND OF THE INVENTION

1. Field of the Invention

The present invention relates to the field of peptides useful for binding to integrin alpha-v-beta-6 ("$\alpha_v\beta_6$") cell surface receptors, and also to the field of biomarkers as cancer diagnostic tools.

2. Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Detection of pancreatic cancer remains a high priority and effective diagnostic and therapeutic tools are needed for clinical applications. Many cancer cells over express integrin $\alpha_v\beta_6$, a cell surface receptor being evaluated as a novel clinical biomarker.

Integrins are a family of heterodimeric cell surface receptors that mediate cellular adhesion to extracellular matrix proteins and serve as bi-directional signal transducers to regulate differentiation, migration, proliferation, and cell death (1, 2). Integrin $\alpha_v\beta_3$ promotes in certain embodiments, a sequence with at least neovascularization (3, 4). However in certain cancers, other integrins, such as $\alpha_v\beta_6$, become highly over expressed on cell surfaces (2, 5, 6). Therefore, this biomarker is being validated for detection of colon, liver, ovarian, pancreatic, and squamous cell cancers (7-9). Molecular imaging of integrin $\alpha_v\beta_6$ may be used to gauge receptor expression levels to determine prognosis and guide therapy (10-12). As described below, potent integrin $\alpha_v\beta_6$ binders for use with radiotracers for early cancer detection were developed.

Several integrin $\alpha_v\beta_6$ binders have been previously identified from natural and combinatorial sources. Linear $\alpha_v\beta_6$-binding peptides derived from the coat protein of foot-and-mouth-disease viruses (FMDV) generally suffered poor in vivo stability, which raise concerns about their potential immunogenicity. $^{64}$Cu-labeled versions of FMDV peptides demonstrated extremely high renal retention, which suggests that these peptides may not be ideal translational candidates. An alternative to radio-metals is the use of radio-halogens (7, 9, 13). Phage display systems have identified several linear and disulfide-cyclized peptides that bind $\alpha_v\beta_6$ (14, 15). In one study, a radio-iodinated linear peptide, HBP-1, showed rapid degradation in serum (16). One-bead-one-compound libraries have identified many binders, of which 43 $^{18}$F-labeled linear peptides were tested in a high throughput live animal imaging survey (17). While some of these peptides showed promising small animal data, linear peptides or even simple disulfide-bonded peptides with stability problems may discourage translation (17). Peptide fragments can be highly immunogenic, thus rendering the parent peptide untranslatable (18). For these reasons, the present invention was developed to generate high-affinity binders that are very stable in physiological media, demonstrate low off target accumulation and effectively detect cancer in living subjects.

Engineered cystine knot peptides (knottins) have shown promise for cancer imaging with $\alpha_v\beta_3$ as a target (19-21). The cystine knot is a rigid molecular scaffold of 3-4 kDa that owes its exceptionally-high stability to three interwoven disulfide bonds and a centrally-located beta sheet. Potent receptor-binding activities have been engineered into the scaffold's solvent exposed loops (22). The knotted structure helps to resist degradation/denaturation in hostile biological, chemical and physical environments such as strong acids and boiling water (23). Cystine knots have shown exceptional structural stability during prolonged incubation in serum (19).

Moreover, their use in humans as uterogenics has not led to reports of adverse side effects, albeit without formal published studies (24, 25). Binding potency remains high for engineered knots that were subjected to long-term storage (>1 year) in water at 4° C. or stored in lyophilized form at room temperature. The N-terminus provides a sole primary amine for site-specific conjugation of imaging labels, bioactive cargo, or pharmacokinetic stabilizers. Collectively, these characteristics bode well for clinical translation.

3. Specific Patents and Publications

US Published Application 2009/0257952, entitled "Engineered Integrin binding Peptides," by Cochran, et al., discloses engineered binding peptides comprised in EETI-II, AgRP, mini-AgRP, agatoxin or miniagatoxin scaffolds. The peptides specifically bind to integrins $\alpha_v\beta_5$ and $\alpha_v\beta_3$ and have an integrin binding XXRGDXXXX sequence. The publication discloses a randomized library of RGD mimic sequences based on different scaffolds. The publication further discloses imaging of various cancers using compounds of the invention and discusses their properties for use as imaging probes.

"Developing New Tools for the in vivo Generation/Screening of Cyclic Peptide Libraries. A New Combinatorial Approach for the Detection of Bacterial Toxin Inhibitors," a research report from Lawrence Livermore Laboratory, published online, UCRL-TR-227590, describes synthesis of MCoTI-II.

Sommerhoff et al., "Engineered Cystine Knot Miniproteins as Potent Inhibitors of Human Mast Cell Tryptase β," J. Mol. Biol. 395:167-175 (8 Jan. 1010) discloses inhibitors derived from a linear variant of the cyclic cystine knot miniprotein MCoTI-II, originally isolated from the seeds of *Momordica cochinchinensis*. A synthetic cyclic miniprotein was prepared that bears additional positive charge in the loop connecting the N- and C-termini.

Kraft S, Diefenbach B, Mehta R, Jonczyk A, Luckenbach G A, Goodman S L., "definition of an unexpected ligand recognition motif for alpha-v-beta-6 integrin," J Biol Chem 1999; 274: 1979-85 discloses the recognition profiles of recombinant alpha-v-beta-6 and alpha-v-beta-3 integrins by using phage display screening employing 7-mer and 12-mer peptide libraries. As predicted, phages binding strongly to alpha-v-beta-3 contained ubiquitous RGD sequences. However, on alpha-v-beta-6, in addition to RGD-containing phages, one-quarter of the population from the 12-mer library contained the distinctive consensus motif DLXXL. A synthetic DLXXL peptide, RTDLDSLRTYTL (SEQ ID NO: 1), selected from the phage sequences (clone-1) was a selective inhibitor of RGD-dependent ligand binding to alpha-v-beta-6 in isolated receptor assays (IC50=20 nM), and in cell adhesion assays (IC50=50 microM).

Dicara et al., "Structure-function analysis of Arg-Gly-Asp helix motifs in alpha v beta 6 integrin ligands," J Biol Chem. 2007 Mar. 30; 282(13):9657-65. Epub 2007 Jan. 23, discloses physical requirements for high affinity binding of ligands to alpha-v-beta-6. By combining a series of structural analyses with functional testing, the authors show that 20-mer peptide ligands, derived from high affinity ligands of alpha-v-beta-6 (foot-and-mouth-disease virus, latency associated peptide), have a common structure comprising an Arg-Gly-Asp motif at the tip of a hairpin turn followed immediately by a C-terminal helix.

BRIEF SUMMARY OF THE INVENTION

The following brief summary is not intended to include all features and aspects of the present invention, nor does it imply that the invention must include all features and aspects discussed in this summary.

In certain aspects, the present invention comprises peptides with high affinity for integrin $\alpha_v\beta_6$ comprised of a knottin scaffold and a binding loop between two cystines in the scaffold. In certain aspects, the present invention comprises peptides substantially identical to peptides designated herein as $R_o1$, $R_o2$, $E_o2$, and S02, as follows:

TABLE 1

Integrin $\alpha_v\beta_6$ Specific Cystine Knots

| | | |
|---|---|---|
| $R_o1$ | GC_*ILNMRTDLGTLLFR*CRRDSDCPGACICRGNGYCG | (SEQ ID NO: 2) |
| $R_o2$ | GC*RSLARTDLDHLRGR*CRRDSDCPGACICRGNGYCG | (SEQ ID NO: 3) |
| $E_o2$ | GC*RSLARTDLDHLRGR*CEEDSDCLAECICEENGFCG | (SEQ ID NO: 4) |
| $S_o2$ | GC*RSLARTDLDHLRDR*CSSDSDCLAECICLENGFCG | (SEQ ID NO: 5) |

In Table 1, cystines linked by disulfide bonds are underlined. The loop 1 region that is modified (not found in the native scaffold) and selected to create peptides that bind with high affinity to integrin $\alpha_v\beta_6$ is between the asterisks. Within the loop, the binding motif RTDL--L (SEQ ID NO: 6, for binding to the integrin) is also underlined. Certain residues outside of loop 1 may be modified without affecting binding ability, as long as the disulfide bond structure is retained. To a lesser degree, residues within the loop may also be modified, particularly those residues not underlined in the above table. The modified peptides may have an amino acid sequence that is at least 30/36 amino acids (83%), at least 32/36 amino acids (88%), or at least 34/36 amino acids (94%) or at least 35/36 amino acids (97%) identical to one of $R_o1$, $R_o2$, $E_o2$ or $S_o2$.

In certain embodiments the loop between the asterisks in $R_o1$ (SEQ ID NO: 2) above may have the sequences:

| | | |
|---|---|---|
| MAR: | ILNRRTDLGTLLFR; | (SEQ ID NO: 60) |
| MAG: or | ILNGRTDLGTLLFR; | (SEQ ID NO: 61) |
| MAW: | ILNWRTDLGTLLFR. | (SEQ ID NO: 62) |

In certain aspects, the present invention comprises a peptide having the following general formula:

(SEQ ID NO: 8)

$$GCX_1\ X_2\ X_3\ X_4\ RTDLX_5\ X_6\ LX_7\ X_8\ RCX_9\ X_{10}\ DSDCX_{11}\ X_{12}\ X_{13}\ CICX_{14}\ X_{15}\ NG\ X_{16}\ CG$$

wherein, $X_1$ is I or R; $X_2$ is L or S; $X_3$ is N or L; $X_4$ is M or A or R or G or W; $X_5$ is G or D; $X_6$ is T or H; $X_7$ is L or R; $X_8$ is F, D or G; $X_9$ is R E or S; $X_{10}$ is R, S, or E; $X_{11}$ is P or L; $X_{12}$ is G or A; $X_{13}$ is A or E; $X_{14}$ is R, E or L; $X_{15}$ is G or E; and $X_{16}$ is Y or F.

The present peptides may be prepared for administration using a pharmacologically acceptable excipient or carrier.

In certain embodiments, the present peptides are useful for molecular imaging. The peptides may comprise a molecular imaging label that is attached to the peptide via a chelating agent, such a DOTA. The label may be a metal or a halogen, such as $^{64}$Cu or $^{18}$F.

In certain aspects, the present invention comprises a method of detecting an alpha-v-beta-6 integrin comprising: (a) contacting the alpha-v-beta-6 integrin with a peptide having a sequence substantially identical to one of the sequences found in Table 1 and (b) detecting binding of the peptide to the alpha-v-beta-6 integrin.

The method of detection may be done in a whole mammal or on tissue removed from a body, i.e. in vitro. The alpha-v-beta-6 integrin may be expressed on a cancer cell wherein the cancer cell is in a tumor, such as pancreatic cancer.

The method also contemplates the use of the present peptides linked to a label useful for positron emission tomography (PET) of tissue expressing alpha-v-beta-6 integrin.

In certain aspects, the present invention also comprises a method of delivering an agent to a cancer cell expressing alpha-v-beta-6 integrin, comprising contacting said cell with a peptide having a sequence substantially identical to one of the sequences found in Table 1 said peptide being linked to said agent. The agent may be selected from the group consisting of a peptide toxin and a radionuclide.

In certain aspects, the present invention also comprises a method of ameliorating or preventing (i.e. "treating") viral infection in an animal at risk for infection with a virus that binds alpha-v-beta-6 integrin, comprising administering to said animal a peptide having a sequence substantially identical to one of the sequences found in Table 1. The subject animal may be a cloven hoof animal and the virus is foot-and-mouth disease virus.

BRIEF DESCRIPTION OF THE DRAWINGS

FIG. 1A is a line graph showing the $K_D$ values of $R_o1$, $R_o2$, and $R_o3$.

FIG. 1B is a line graph illustrating the $K_D$ values of $S_o1$, $S_o2$, and $S_o3$.

FIG. 1C is a bar graph showing that the peptides demonstrate very low binding to integrins $\alpha_v\beta_3$, $\alpha_v\beta_5$ and $\alpha_5\beta_1$.

FIG. 2A is a bar graph showing different binding peptides and their specificity to their targets.

FIG. 2B is a bar graph illustrating dose dependent inhibition indicated competition between peptides for a specific target-binding site.

FIG. 2C is a bar graph showing cells that express native integrin $\alpha_v\beta_6$.

FIG. 2D is a bar graph showing peptides $R_o1$ and $S_o2$ blocked adhesion of BxPC-3 cells onto A20 coated wells confirming specific binding between peptides and functionally-active integrins expressed on cellular surfaces. (A20 is a control peptide derived from the envelope protein of foot-and mouth disease and has an IC50 of 3+/−1 nM for integrin $\alpha_v\beta_6$).

FIG. 3A is a bar graph showing binding specificity of scrambled peptides $scR_o1$ and $scS_o2$ and positive control $R_o2$ that was measured using 100 nM and 300 nM integrin $\alpha_v\beta_6$ for the scrambled peptides and 1 nM integrin $\alpha_v\beta_6$ for $R_o2$, which were normalized to unity.

FIG. 3B is a bar graph showing the relative binding of the integrin $\alpha_v\beta_6$.

DETAILED DESCRIPTION OF THE PREFERRED EMBODIMENT

Definitions

Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The abbreviation "AHA" as used herein refers to 6-aminohexanoic acid that was used as a linker to couple peptide A20 to biotin.

The abbreviation "BMGY" as used herein refers to Buffered Complex Glycerol Media (Invitrogen).

The abbreviation "BMMY" as used herein refers to Buffered Complex Methanol Media (Invitrogen).

The term "DIEA" as used herein refers to diisopropylethylamine (Sigma).

The term "DMEM" as used herein refers to Dulbecco's Modified Eagle Medium.

The term "DOTA" as used herein refers to 1,4,7,10-tetraazacyclododecane-1,4,7,10-tetraacetic acid, a common chelator agent used for $^{64}CU^{2+}$ PET imaging (Macrocyclics).

The term "FBS" as used herein refers to fetal bovine serum.

The abbreviations "h" and "min" as used herein refer to hour(s) and minute(s).

The term "MALDI-MS" as used herein refers to matrix-assisted laser desorption/ionization time-of-flight mass spectroscopy.

The term "NHS" as used herein refers to N-hydroxysuccinimide, which activates carboxyl groups for chemical conjugation with amine groups.

The term "IBB" as used herein refers to integrin binding buffer, which is composed of 25 mM TRIS pH 7.5 containing 150 mM NaCl, 1 mg/ml BSA and 1 mM each of $Ca^{2+}$, $Mg^{2+}$ and $Mn^{2+}$.

The term "PCR" as used herein refers to polymerase chain reaction.

The term "PBS" as used herein refers to phosphate buffered saline.

The term "% ID/g" as used herein refers to the radiotracer, which is "percent injected dose per gram of tissue".

The term "p.i." as used herein refers to imaging time points, p.i. means "post injection".

The term "RDB" as used herein refers to Regeneration Dextrose Medium (Invitrogen)

The term "ROI" as used herein refers to the region of interest when performing image analysis. Often, a circle is drawn around a region such as the tumor. A software program such as ASIPro VM (Siemens) quantifies signal counts emanating from the region of interest.

The term "SD" as used herein refers to Standard Deviation.

Figure 5:
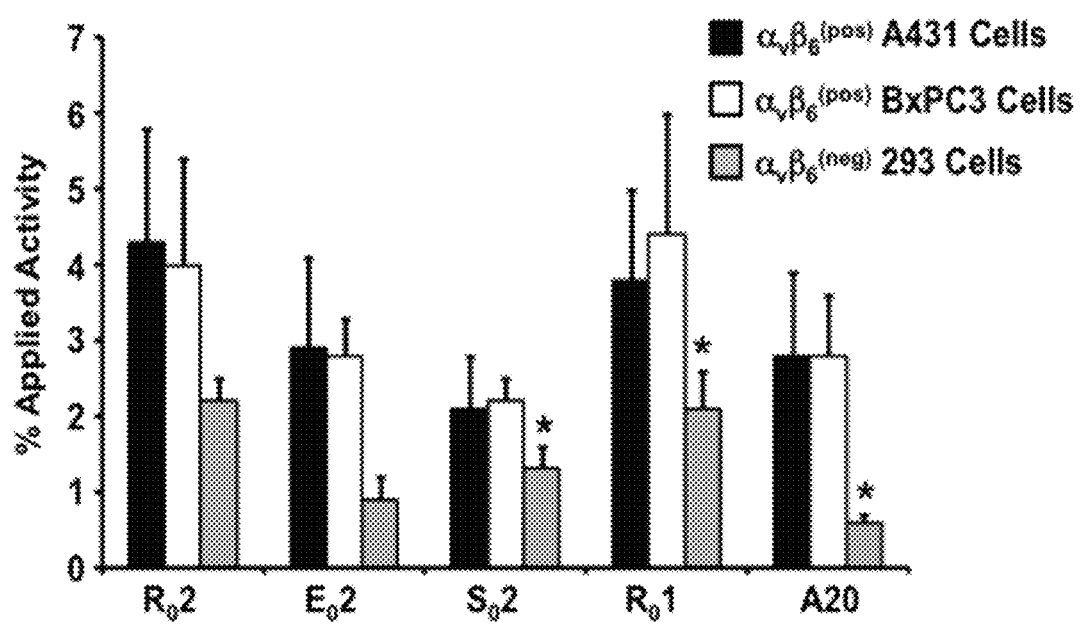
FIG. 5 is a bar graph illustrating cell uptake assays which determined the amount of $^{64}$Cu-DOTA labeled peptides taken up by cells that express integrin $\alpha_v\beta_6$, A431 cells (black) and BxPC-3 (white), and the non-expressing 293 cells (grey). Asterisks indicate significantly (p<0.05, n=3) less radiotracer uptake by the integrin $\alpha_v\beta_6$-negative cells line, 293 (grey bars) compared to BxPC-3 cells.

The term "T+ and T−" as used herein refer to tumors that express integrin $\alpha_v\beta_6$ (BxPC-3) and tumor that do not (293), respectively (FIG. 5).

The term "TFA" as used herein refers to trifluoracetic acid (Fisher).

The term "293" as used herein refers to HEK-293T cells.

The terms "X" and "NNB" are used herein in some instances to refer to loop positions denoted by "X", where the positions are randomized positions, which define the biocombinatorial library. "X" refers to any amino acid. Each "X" in a randomized loop is encoded by the "NNB" codon set, where "N" is the universal representation for a nucleotide mixture consisting of an equal portion of A,T,C and G (25% each). The universal codon "B" is 33% mixture of the bases C, G and T.

The term "specific binding affinity" as used herein refers to a property of a peptide as having an equilibrium dissociation constant (KD) for a particular ligands (i.e. alpha-v-beta-6 integrin, as shown in FIG. 1) that is significantly higher than a peptide that shows no specific binding to the target. Specific binding activity of the present peptides will generally be in the range of about 1-10 nM, or 2-9 nM, measured as described in detail below.

The term "substantial identity" as used herein refers to, in the context of a peptide, a peptide which comprises, in certain embodiments, a sequence with at least 70% sequence identity to a reference sequence, in certain embodiments, a sequence with at least 80%, in certain embodiments, a sequence with at least about 85%, (including 83%) in certain embodiments, a sequence with at least about 90% (including 88%) or in certain embodiments, a sequence with at least at least about 95% (including 94%) sequence identity to the reference sequence over a specified comparison window, which in this case is either the entire peptide, a molecular scaffold portion, or a binding loop portion (between asterisks in Table 1). Preferably, optimal alignment is conducted using the homology alignment algorithm of Needleman and Wunsch (1970) J. Mol. Biol., 48:443 453. Another indication that two peptide sequences are substantially identical is that one peptide is immunologically reactive with antibodies raised against the second peptide.

Another indication, for present purposes, that a sequence is substantially identical to a specific sequence explicitly exemplified, is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified, e.g., by the PAM 250 scoring matrix. Peptides that are "substantially similar" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (http://helixweb.nih.gov/multi-align/). Three-dimensional tools may also be used for sequence comparison.

The term "scaffold portion" as used herein refers to a portion of a peptide that forms a molecular scaffold, as described in detail above. Briefly, a scaffold portion of a peptide gives three dimensional rigidity to a binding portion within the scaffold portion, e.g. between two linked cysteine residues. The present peptides consist of a scaffold portion and a loop portion.

The term "percentage of sequence identity" as used herein means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "chelator" as used herein refers to a chemical moiety that binds noncovalently to, or complexes with, one or more ions. Chelators can bind to lithium, calcium, sodium, magnesium, potassium, and/or other biologically important metal ions. The binding of the chelator to an ion can be determined by measuring the dissociation constant between a chelator and an ion. According to the invention, the dissociation constant $K_D$ between the chelator and the ion is from about $10^{-3}$ to about $10^{-15 M.-1}$. Preferably, the dissociation constant $K_D$ between the chelator and the ion is from about $10^{-6}$ to about $10^{-15}$ M.−1.

Examples of chelators are well known in the art. Preferably, the chelator binds a metal cation. Suitable chelators are bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; $(C_6H_5)_2 PCH_2 CH_2 P(C_6H5)_2$ (diphos); glyme; diglyme; bis(acetylacetonate) ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11- tetraazacyclotetradecanetetraacetic acid (TETA), DOTA-N-(2-aminoethyl) amide; DOTA-N-(2-aminophenethyl) amide; and 1,4,8,11-tetraazacyclotetradecane.

The term "radiolabel" as used herein means a radioactive or paramagnetic substance attached to the probe either directly or through a chelator, and attached in sufficient quantity and activity to generate a signal in an organism, including a human. That is, the radiolabel forms part of the chemical structure of the inhibitor and is a radioactive or non-radioactive isotope present at a level significantly above the natural abundance level of said isotope. Such elevated or enriched levels of isotope are suitably at least 5 times, preferably at least 50 times the natural abundance level of the isotope in question, or present at a level where the level of enrichment of the isotope in question is 90 to 100% of the total quantity of radiolabel attached. Radiolabels may include $CH_3$ groups on the present probes with elevated levels of 13 C or 11 C and fluoroalkyl groups with elevated levels of $^{18}F$, such that the radiolabel is the isotopically labeled $^{13}C$, $^{11}C$ or $^{18}F$ within the chemical structure of the probe. Preferred radiolabels are those which can be detected externally in a non-invasive manner following administration in vivo. The radiolabel is preferably chosen from: (i) a radioactive metal ion; (ii) a paramagnetic metal ion; (iii) a gamma-emitting radioactive halogen; (iv) a positron-emitting radioactive non-metal; and (v) a hyperpolarised NMR-active nucleus.

Most preferred radiolabels are radioactive, especially radioactive metal ions, gamma-emitting radioactive halogens and positron-emitting radioactive non-metals, particularly those suitable for imaging using SPECT or PET. These labels include radioactive transition elements plus lanthanides and actinides, and metallic main group elements. The semi-metals arsenic, selenium and tellurium are excluded from the scope. Suitable radiometals can be either positron emitters such as $^{64}Cu$, $^{48}V$, $^{52}Fe$, $^{55}Co$, $^{94m}Tc$ or $^{68}Ga$; or γ-emitters such as $^{99m}Tc$, $^{111}In$, $^{113m}In$, $^{67}Cu$ or $^{67}Ga$. Preferred radiometals are $^{99m}Tc$, $^{64}Cu$, $^{68}Ga$ and $^{111}In$. Most preferred radiometals are γ-emitters, especially $^{99m}Tc$.

When the radiolabel is a paramagnetic metal ion, suitable such metal ions include: Gd (III), Mn (II), Cu (II), Cr (III), Fe (III), Co (II), Er (II), Ni (II), Eu (III), or Dy (III). Preferred paramagnetic metal ions are Gd (III), Mn (II), and Fe (III), with Gd (III) being especially preferred.

When the radiolabel is a gamma-emitting radioactive halogen, the radiohalogen is suitably chosen from $^{123}I$, $^{125}I$, $^{131}I$, or $^{77}Br$. A preferred gamma-emitting radioactive halogen is $^{125}I$.

When the radiolabel is a positron-emitting radioactive non-metal, suitable such positron emitters include: $^{11}C$, $^{13}N$, $^{17}F$, $^{18}F$, $^{75}Br$, $^{76}Br$, or $^{124}I$. Preferred positron-emitting radioactive non-metals are $^{11}C$, $^{13}N$, $^{124}I$ and $^{18}F$, especially $^{11}C$ and $^{18}F$, most especially $^{18}F$.

The term "Integrin $\alpha_v\beta_6$" as used herein refers to a member of the integrin family having the alpha-v subunit and the beta-6 subunit. Integrins are a family of cell surface receptors that mediate cell-cell and cell-extracellular matrix adhesion in various cell types including epithelial keratinocytes. These receptors are heterodimeric transmembrane glycoproteins composed of an alpha (α) and beta (β) subunit. The integrin alpha-5 subunit has been cloned in a number of species. Of particular importance is the human alpha-5 subunit, GenBank Accession No. NP_071417.2. The sequence of the human beta-6 subunit may be found at GenBank Accession NP_000879.2. Integrin $\alpha_v\beta_6$ is known to bind fibronectin and TGFβ1+3. It is found in proliferating epithelial cells. The integrin $\alpha_v\beta_6$ is selectively expressed in many carcinomas, and it has been shown that it promotes tumor cell invasion, and can also modulate a fibrotic stromal response through its ability to activate TGF-beta-1. Further description of $\alpha_v\beta_6$ may be found in U.S. Pat. No. 7,943,742 entitled "Anti-$\alpha_v\beta_6$ antibodies and uses thereof."

The term "knottin" as used herein refers to peptides that are identified by commonly accepted UniProt or GenBank names. The amino acid sequences of each of these knottins are given in these databases, along with other information. For example, "McoTI" I and II refer to MCoTI-I Trypsin inhibitor I and II, respectively; LCTI-II is an alternative name for UNiProt entry ITR2-LUFCY. BDTI-II is Trypsin inhibitor II, UNiProt entry P11968; MRTI-I is UniProt entry P17680; MCTI-II is UniProt p10295; CMTI's can be found under UniProt P32041; Q9S8W3; Q9S8W2, or GenBank ITR4-CUCMA; CPTI-II may be found at UniProt P10293; EETI-II may be found at UniProt P12071; MCTI-III may be found at UniProt Q9S747; CMCTI-III may be found at UniProt Q9S8W2; CMCTI-I may be found at UniProt P32041; CSTI-IV may be found at UniProt P10292; CSTI-IIB may be found at UniProt P10291; LCTII-IV may be found at UniProt Q8W4Y8; P25849; P25850; and Q9S812. As shown in Example II, these knottins are tyrpsin inhibitors and have specific sequence homologies, as well as common secondary and tertiary structures. They are characterized by a "disulfide through disulfide knot."

Overview

The present invention concerns the development of new cystine knot-based peptides that bind to integrin $\alpha_v\beta_6$. They are shown to bind to integrin $\alpha_v\beta_6$ expressed on human pancreatic tumors grown in mice. Highly stable cystine knot peptides with potent and specific integrin $\alpha_v\beta_6$ binding activities for cancer detection have been created. Pharmacokinetic engineering of a scaffold primary sequence led to significant decreases in off-target radiotracer accumulation. Specifically, it is disclosed that R and E may be removed, and high renal clearance amino acids such as S (or H or Q or L or G) may be added. Optimization of binding affinity, specificity, stability and pharmacokinetics facilitates use of cystine knots for cancer molecular imaging. To validate this molecular target, several highly stable cystine knot peptides were created by directed evolution to bind specifically and with high-affinity (3-6 nM) to integrin $\alpha_v\beta_6$. These peptides don't cross-react with related integrin $\alpha_v\beta_5$, integrin $\alpha_5\beta_1$ or tumor-angiogenesis associated integrin, $\alpha_v\beta_3$.

Described also is the engineering and validation of new peptide-radiotracers for integrin $\alpha_v\beta_6$. Currently, radiotracers that specifically detect pancreatic cancers are clinically unavailable. Targeting of integrin $\alpha_v\beta_6$ was validated using various models described below. The present peptides utilize the $\alpha_v\beta_6$ binding motif RTDLXXL (SEQ ID NO: 6), grafted onto a linearized cyclic knottin scaffold (e.g. McoTI-II). The present peptides show high-affinity (nanomolar) and specificity for integrin $\alpha_v\beta_6$, with no cross reactivity to related integrins $\alpha_v\beta_3$, $\alpha_v\beta_5$ and $\alpha_5\beta_1$. Uptake of the radiotracers by integrin $\alpha_v\beta_6$-expressing tumors was rapid and high (~2-5 percent injected dose per gram, 1 hour post injection).

The pharmacokinetics of the present peptides have been optimized to minimize off-target background. In contrast to linear peptides, these disulfide-stabilized radiotracers are much more stable in serum, blood and urine and may therefore be less immunogenic. The cystine knot class of peptides has an extremely long shelf life in dry or solvated forms. The sole N-terminus primary amine enables site-specific conjugation of radiometals or radiohalogens. Together, these characteristics indicate potential for clinical application.

Peptide Structures

The present scaffolds (designated $R_0$, $E_0$) are based on "constant" or "scaffold" regions of *Momordica cochinchinensis* Trypsin Inhibitor-II (MCoTI-II) from squash, and on constant regions found in the LCTI subfamily ($S_0$, $E_{1-4}$). However, this scaffold shares significant homology with other naturally occurring trypsin-inhibitor cystine knot peptides, such as EETI-II. MoCoTI-II and MoCOTI-I are backbone cyclized through loop 6 (i.e. the end G is linked to V).

The present sequences may be entered into the knottin database (http (colon slash slash) knottin.cbs.cnrs.fr/) and homologies to various portions of the knottin will be found. Thus, as described below, the present sequences may be modified by substituting, altering, inserting or deleting a small number of amino acids in the sequences given in Table 1, according to the guidance provided here.

As described below, yeast surface display and high throughput screening by FACS produced many high-affinity binders that selectively accumulate in $\alpha_v\beta_6$-positive pancreatic and epidermoid cancer models, but not in $\alpha_v\beta_6$-negative tumors actively growing in mice. By grafting the loop known as activity "2" (RSLARTDLDHLRGR-bolded below (SEQ ID NO: 7)) across different cystine knot scaffolds with biased amino acid content ($R_0$, $E_0$ and $S_0$, Table 1), there was significantly lower renal signal without compromising $\alpha_v\beta_6$ binding affinity or specificity. It is suggested that primary sequence composition drives pharmacokinetics, so that it may be possible to optimize tumor uptake, tumor-to-muscle contrast and off-target accumulation in tissues by fine-tuning the non-target-binding portions of the scaffold in addition to engineering target-binding loops.

The peptides from Table 1 have a consensus sequence that can be illustrated with respect to $R_0$1 as follows:

```
                                       (SEQ ID NO: 2)
R01     GCilnmRTDLgtLlfRCrrDSDCpgaCICrgNGyCG 36
```

The small letters show residues that are not 100% conserved among all four peptides, and thus are likely candidates for substitution in various embodiments of the present invention. Twenty of the 36 amino acids are conserved, which may be regarded as 20/36 or 55.5% identity.

Thus, the present peptides may be represented according to the formula:

(SEQ ID NO: 8)

$GCX_1\ X_2\ X_3\ X_4\ RTDLX_5\ X_6\ LX_7\ X_8\ RCX_9\ X_{10}\ DSDCX_{11}\ X_{12}\ X_{13}\ CICX_{14}\ X_{15}\ NG\ X_{16}\ CG$ wherein each of $X_1$ through $X_{16}$ independently is selected from a corresponding amino acid in one of $R_0$1, $R_0$2, $E_0$2 and $S_0$2, for example: $X_1$ may be I or R; $X_2$ may be L or S; $X_3$ may be N or L; X4 may be M or A; as described in connection with MΔR, MΔG, and MΔW, X4 may also be R, G, or W. $X_5$ may be G or D; $X_6$ may be T or H; $X_7$ may be L or R; $X_8$ may be F, D or G; $X_9$ may be R, E, or S; $X_{10}$ may be R, S, or E; $X_{11}$ may be P or L; $X_{12}$ may be G or A; $X_{13}$ may be A or E; $X_{14}$ may be R, E or L; $X_{15}$ may be G or E; and $X_{16}$ may be Y or F.

In certain embodiments, X1 may be R; X2 may be S; X3 may be L; X4 may be A; X5 may be D; X6 may be H; X7 may be R; X8 may be F, D or G; and X9 may be R, E, or S. In certain embodiments, the peptide may be as set forth in the preceding sentence, except that X4 may be one of R, G and W.

In these embodiments, amino acids not defined may be specified as set forth in SEQ ID NO: 2.

PET Imaging

Positron emission tomography showed that these disulfide-stabilized peptides rapidly accumulate at tumors expressing integrin $\alpha_v\beta_6$. Clinically relevant tumor-to-muscle ratios of 7.7±2.4 to 11.3±3.0 were achieved within one hour after radiotracer injection. Minimization of off-target dosing was achieved by reformatting $\alpha_v\beta_6$ binding activities across various natural and pharmacokinetically-stabilized cystine knot scaffolds with different amino acid content. It was demonstrated that a peptide scaffold's primary sequence directs its pharmacokinetics. Scaffolds with high arginine or glutamic acid content suffered high renal retention of >75 percent injected dose per gram (% ID/g). Substitution of these amino acids with renally-cleared amino acids, notably serine, led to significant decreases in renal accumulation of <20% ID/g 1 h post injection ($p<0.05$, $n=3$).

Absolute $^{64}$Cu-DOTA signal intensity at the tumor was greatest for the two $R_0$ binders, $R_0$1 and $R_0$2 (~4.5% ID/g at 1 h p.i.). $^{64}$Cu-DOTA-labeled $E_0$2, $S_0$2 and A20 generated approximately half the tumor signal intensity compared to the R-rich scaffolds. Given the similar affinities of the engineered knots (FIG. 1A, 1B), it was rationalized that $R_0$s' higher tumor signal benefited from the inherent "stickiness" of arginine. However, independent of a scaffold's compositional differences, each of the activity "2" knots ($R_0$2, $E_0$2, and $S_0$2) demonstrated similarly useful tumor-to-normal contrast enabling precise delineation of integrin $\alpha_v\beta_6$-positive tumors (T+) from $\alpha_v\beta_6$-negative tumors (T−).

For clinical imaging of pancreatic cancer, $S_0$2 emerged as the lead candidate. $^{64}$Cu-DOTA-$S_0$2 demonstrated an excellent tumor-to-background ratio (~10 at 1 h), rapid renal clearance (~25% ID/g 1 h p.i. to <10% ID/g after 24 h), and high serum stability (>95% after 24 h). In contrast, $^{64}$Cu-DOTA-$R_0$2 rapidly degrades in serum (<20% intact 24 h) and accumulates to a much higher degree in the kidneys (~75% ID/g 1 h). $^{64}$Cu-DOTA-$E_0$2 also suffers from prolonged and high renal retention (~75% ID/g 1 h). Therefore, to take advantage of $S_0$s' lower renal background, affinity maturation was performed to achieve higher tumor uptake comparable to $R_0$ binders. $^{18}$F-labeling strategies were also explored since the pharmacokinetics of these binders support a shorter lived isotope for clinical translation.

Biodistribution studies indicated that $^{64}$Cu-DOTA-$S_0$2 also effectively accumulated in orthotopic pancreatic tumors (~1.8% ID/g 1 h p.i.) compared to normal pancreas (~0.2-0.3% ID/g). However, tumor-to-liver/kidney/gut ratios were suboptimal (Table 2A, 2B). The proximity of these PET-avid tissues is ~1-3 mm from the pancreas and is beyond the spatial resolution of the PET scanner. Therefore, definitive identification of orthotopic tumors by PET was limited by closely-packed mouse organs. However, human scanning should not suffer from these limitations.

TABLE 2A

Biodistribution of $^{64}$Cu-DOTA-labeled peptides in $\alpha_v\beta_6$-positive BxPC-3 pancreatic tumor models Data are presented as mean % ID/g ± SD

| Tissue | $^{64}$Cu-DOTA-R$_0$1 | | $^{64}$Cu-DOTA-S$_0$2 | | $^{64}$Cu-DOTA-S$_0$2 (*) | |
|---|---|---|---|---|---|---|
| | 1 h | 24 h | 1 h | 24 h | 1 h | 24 h |
| Tumor | 4.13 ± 1.01 | 3.31 ± 0.20 | 1.80 ± 0.50 | 1.46 ± 0.43 | 1.85 ± 0.11 (*) | n.d. |
| Muscle | 0.49 ± 0.21 | 0.33 ± 0.14 | 0.24 ± 0.14 | 0.14 ± 0.02 | 0.21 ± 0.02 | n.d. |
| Blood | 0.46 ± 0.18 | 0.52 ± 0.09 | 0.29 ± 0.07 | 0.23 ± 0.03 | 0.22 ± 0.03 | n.d. |
| Heart | 0.39 ± 0.08 | 0.67 ± 0.12 | 0.22 ± 0.04 | 0.47 ± 0.03 | 0.32 ± 0.01 | n.d. |
| Kidney | 68.12 ± 9.69 | 33.75 ± 1.77 | 26.53 ± 12.26 | 10.69 ± 1.63 | 31.49 ± 2.47 | n.d. |
| Liver | 2.28 ± 0.40 | 4.69 ± 0.75 | 3.03 ± 1.10 | 2.79 ± 0.65 | 2.70 ± 0.53 | n.d. |
| Lung | 2.78 ± 0.59 | 2.34 ± 080 | 1.03 ± 0.29 | 1.22 ± 0.50 | 0.95 ± 0.09 | n.d. |
| Spleen | 0.52 ± 0.18 | 0.67 ± 0.11 | 0.27 ± 0.12 | 0.36 ± 0.13 | 0.39 ± 0.09 | n.d. |
| Pancreas | 0.57 ± 0.10 | 0.73 ± 0.28 | 0.17 ± 0.02 | 0.25 ± 0.02 | orthotopic (*) | n.d. |
| Stomach | 2.31 ± 0.12 | 2.71 ± 0.42 | 0.79 ± 0.19 | 0.98 ± 0.27 | 1.51 ± 0.11 | n.d. |
| Intestine | 1.49 ± 0.2 | 2.05 ± 0.38 | 1.280.26 | 0.92 ± 0.27 | 1.05 ± 0.11 | n.d. |
| Brain | 0.07 ± 0.01 | 0.15 ± 0.03 | 0.04 ± 0.01 | 0.07 ± 0.01 | 0.06 ± 0.01 | n.d. |
| Bone | 0.26 ± 0.08 | 0.510.24 | 0.09 ± 0.01 | 0.19 ± 0.06 | 0.23 ± 0.01 | n.d. |
| Skin | 0.99 ± 0.14 | 1.04 ± 0.72 | 0.34 ± 0.09 | 0.66 ± 0.15 | 0.46 ± 0.32 | n.d. |

TABLE 2B

Tumor-to-Normal Tissue Ratios

| Ratio | $^{64}$Cu-DOTA-R$_0$1 | | $^{64}$Cu-DOTA-S$_0$2 | | $^{64}$Cu-DOTA-S$_0$2 (*) | |
|---|---|---|---|---|---|---|
| | 1 h | 24 h | 1 h | 24 h | 1 h | 24 h |
| T/Muscle | 8.89 ± 2.00 | 6.52 ± 0.83 | 6.22 ± 0.93 | 6.36 ± 1.20 | 8.54 ± 1.23 | n.d. |
| T/Blood | 9.72 ± 3.63 | 10.81 ± 3.31 | 9.98 ± 5.95 | 10.68 ± 3.44 | 8.86 ± 1.38 | n.d. |
| T/Liver | 1.91 ± 0.85 | 0.72 ± 0.11 | 0.67 ± 0.32 | 0.53 ± 0.19 | 0.70 ± 0.09 | n.d. |
| T/Lung | 1.48 ± 0.12 | 1.54 ± 0.53 | 1.89 ± 0.81 | 1.26 ± 0.28 | 1.95 ± 0.28 | n.d. |
| T/Spleen | 8.34 ± 2.14 | 5.05 ± 0.73 | 7.22 ± 2.26 | 4.23 ± 1.62 | 6.81 ± 2.54 | n.d. |
| T/Pancreas | 7.18 ± 0.55 | 4.96 ± 1.75 | 10.89 ± 3.95 | 5.96 ± 2.20 | orthotopic(*) | n.d. |
| T/Kidneys | 0.06 ± 0.02 | 0.10 ± 0.01 | 0.07 ± 0.03 | 0.14 ± 0.06 | 0.06 ± 0.01 | n.d. |

The engineered knots exhibit specific binding to integrin $\alpha_v\beta_6$. They do not bind related integrins $\alpha_v\beta_3$, $\alpha_v\beta_5$ or $\alpha_5\beta_1$, and the scrambled (RDTLXXL (SEQ ID NO: 9)) versions do not bind $\alpha_v\beta_6$ even at high concentrations (FIGS. 1C, 2A, and 3A). Low uptake of $\alpha_v\beta_6$-specific radiotracers by 293 xenografts correlated to their limited expression of both the alpha-v and beta-6 integrin subunits. In a very clear example, $^{64}$Cu-DOTA-S$_0$2 specificity was demonstrated in a mouse bearing both BxPC-3 and 293 xenografts. Here, signal intensity for the $\alpha_v\beta_6$-positive tumor (T+, left shoulder) was ~2% ID/g, vs. ~0.5% ID/g for the $\alpha_v\beta_6$-negative tumor (T−, right shoulder) tumors at 1 h p.i. The "stickier" R$_0$ binders also demonstrated selectivity for integrin $\alpha_v\beta_6$ expressing cells/tumors and recombinant protein (FIGS. 1, 2). However, muscle wash-out was slower for the R$_0$s', so that contrast was comparable across all binders tested.

Renal clearance can potentially be controlled and optimized. The present invention provides insight about the significant differences in renal uptake reported for peptides previously engineered to bind integrin $\alpha_v\beta_3$, a vascular target (19). Knottins 2.5D and 2.5F, based on the cystine knot *Ecballium elaterium* Trypsin Inhibitor (EETI-II), contain a minimal number of arginines. The renal signals of $^{64}$Cu-DOTA-2.5D and -2.5F measured <10% ID/g from 1-24 h. In contrast, $^{64}$Cu-DOTA-AgRP-7C, derived from the agouti related peptide, which contains many complex nitrogen- and oxygen-containing residues, demonstrated significantly higher renal retention of >65% ID/g at the same time points (29). Renal uptake of radio-metal labeled affibodies has also been reported to be very high (>100% ID/g) at multiple time points for binders 002, 1907 and 2377 (33-35). Affibody sequence inspection reveals the presence of many K, D/E and Q/N residues, which can contribute to high renal retention (36-38). The kidneys appear to actively survey for the more-complex, charge-rich amino acids (D/E/K/R) while allowing rapid clearance of the simpler non-charged amino acids (e.g., A, G, S). The development of stable, pharmacokinetically-optimized scaffolds is highly desirable. The results suggest one way to gain precise control over binder pharmacokinetics.

In summary, cystine knots are inherently stable scaffolds that are potentially well-suited for clinical molecular imaging. Loop-grafting and directed evolution experiments generated single-digit nanomolar binders. PET imaging studies produced clinically useful tumor-to-normal contrast within 1 h. It has been presently demonstrated that simple scaffold swapping could enhance knot stability and stabilize pharmacokinetics to evade renal surveillance and approach renal-stealth. Importantly, most knots are very well-behaved during long-term storage. Collectively, these data suggest that cystine knots warrant further exploration for clinical translation.

Also, as described below, $^{18}$F-fluorobenzoate was used as a PET label.

Formulations, Kits and Other Methods of Use

The present $\alpha_v\beta_6$ targeting peptides may combined with a label and used as imaging agents, as exemplified by $^{18}$F-labeling and microPET imaging of pancreatic tumors in mice. The present imaging agents may be administered to human subjects by mouth, enema, or injection into a vein, artery, or body cavity. The agents are typically absorbed by the body or passed out of the body in the urine or bowel movement. The present agents may be formulated for intravenous administration. For such purpose, the peptide is purified, labeled, repurified to remove unbound label, and dissolved in parenteral fluids such as D5W, distilled water, saline or PEG and adjusting the pH of this solution between 6.8-8.

The present peptides targeting $\alpha_v\beta_6$ may also be used for therapeutic purposes, in that the target integrin plays an important role in physiological processes and disorders (for example inflammation, wound healing and tumors) in which epithelial cells are involved. It is furthermore known that $\alpha_v\beta_6$ integrin also plays a role in the intestinal epithelium, and consequently corresponding integrin agonists/antagonists could be used in the treatment of inflammation, tumors and wounds of the stomach/intestinal tract. A description of other potential uses for inhibiting integrin $\alpha_v\beta_6$ may be found in U.S. Pat. No. 7,632,951.

The present peptides may also be used for diagnostic purposes, in that $\alpha_v\beta_6$ is known as a prognostic biomarker for non-small cell lung cancer, as described in Elayadi A N, Samli K N, Prudkin L, Liu Y H, Bian A, Xie X J, et al. "A peptide selected by biopanning identifies the integrin alphavbeta6 as a prognostic biomarker for nonsmall cell lung cancer." Cancer Res 2007; 67: 5889-95. In this application, formalin-fixed and paraffin-embedded tissue histology sections are deparaffinized and prepared for staining with the present peptides. Uptake of the present peptides may be determined by a label attached to the peptide, or by a secondary antibody prepared to specifically bind to the peptide used.

An antibody binding specifically to one of the presently disclosed peptides may be prepared in monoclonal or polyclonal form, by means known in the art, once the peptide is in hand. Exemplary methods may be found, e.g. in Ashkenazi et al. U.S. Pat. No. 6,252,051, issued Jun. 26, 2001, entitled "Method for making monoclonal antibodies and cross-reactive antibodies obtainable by the method," Kung et al. and U.S. Pat. No. 4,691,010, issued Sep. 1, 1987, entitled "Hybrid cell line for producing monoclonal antibody to a human early thymocyte antiogen, antibody and methods," etc.

As described below, the present peptides are useful in targeting pancreatic cancer. As such, they may be coupled to a toxic agent for selectively inhibiting or destroying pancreatic cancer cells. Toxins known for use for coupling to antibodies may be coupled to the present peptides, such as ricin and diptheria toxin. Cytotoxic radionuclides, such as $^{131}$I or $^{90}$Y may also be coupled to the present peptides, using the conjugation chemistry described herein, or other conjugation methods.

The present peptides may also be combined with other treatment modalities. For example, the present peptides, coupled to a cytotoxic agent, may be administered in conjunction with gemcitabine for treatment of advanced pancreatic cancer. Another option is a combination of chemo drugs called FOLFIRINOX. This consists of four drugs: 5-FU, leucovorin, irinotecan, and oxaliplatin.

The present peptides may be formulated in a pharmacologically acceptable excipient or carrier. Suitable preparations for administering the present peptides include, for example, tablets, capsules, suppositories, solutions, powders, etc. The content of the peptides should be in the range from 0.05 to 90 wt.-%, preferably 0.1 to 50 wt.-% of the composition as a whole. Suitable tablets may be obtained, for example, by mixing the active peptide(s) with known excipients, for example, inert diluents such as calcium carbonate, calcium phosphate, or lactose, disintegrants, such as corn starch or alginic acid, binders such as starch or gelatin, lubricants, such as magnesium stearate or talc and/or agents for delaying release, such as carboxymethyl cellulose, cellulose acetate phthalate, or polyvinyl acetate. The tablets may also comprise several layers.

Suitable fluid carrier components are physiologically compatible diluents wherein the active agents can be dissolved or suspended. An example of a diluent is water, with or without addition of electrolyte salts or thickeners. If the peptides are present in a mixture with physiologically acceptable excipients, the following physiologically acceptable excipients may be used to prepare formulas according to the invention: monosaccharides (e.g., glucose or arabinose), disaccharides (e.g., lactose, saccharose, or maltose), oligo- and polysaccharides (e.g., dextrans), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates.

Preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Further description of formulations adaptable for use with the present peptides may be found in U.S. Pat. No. 7,884,181, entitled "Pharmaceutical formulation comprising crystalline insulin and dissolved insulin."

In another embodiment of the present invention, the present peptides may be formulated for use as a therapeutic agent that blocks binding of an unwanted ligand to the alpha v beta 6 receptor. The alpha v beta 6 receptor is, for example, a known receptor for the foot-and mouth disease virus. See, for details, O'Donnell et al. "Analysis of foot-and-mouth disease virus integrin receptor expression in tissues from naïve and infected cattle," J Comp Pathol. 2009 August-October; 141(2-3):98-112. Epub 2009 Jun. 9. It has been suggested that alpha v beta 6 is the major receptor for the FMD virus (Weinreb et al., "The αvβ6 integrin receptor for Foot-and-mouth disease virus is expressed constitutively on the epithelial cells targeted in cattle," J Gen Virol October 2005 vol. 86 no. 10 2769-2780). There are seven different types and more than 60 subtypes of FMD virus, and there is no universal vaccine against the disease. Vaccines for FMD must match to the type and subtype present in the affected area.

Thus, FMD could be prevented or ameliorated by administration to an at-risk animal (e.g. cow, pig, sheep, goat, etc.) of an alpha V beta 6-blocking peptide according to the present invention. The peptide is formulated for veterinary use, i.e. based on the animal's size and metabolism.

The alpha V beta 6 integrin has also been shown to be a receptor for Coxsackie virus A9, a common human pathogen. See, Williams et al. "Integrin alpha v beta 6 is an RGD-dependent receptor for coxsackievirus A9," J. Virol. 2004 July;78(13):6967-73. Coxsackievirus A9 (CAV9), a member of the *Enterovirus* genus of Picornaviridae, is a common human pathogen and is one of a significant number of viruses containing a functional arginine-glycine-aspartic acid (RGD) motif in one of their capsid proteins.

In this embodiment, the knottin peptide is prepared for oral, intravenous, or, preferably, administration in inhalable form, to protect epithelial cells in the nasopharyngeal, respiratory, oropharyngeal mucosa, etc.

MATERIALS AND METHODS USED IN EXAMPLES

Materials, Cell Lines, and Reagents

BxPC-3 pancreatic cancer cells were obtained from American Type Culture Collection (ATCC) and grown in RPMI 1640 media (ATCC). A431 epidermoid cancer cells, human embryonic kidney 293T cells (293), U87MG (malignant glioma) and MDA-MB-435 (breast cancer) cells were obtained from frozen lab stocks and grown in DMEM supplemented with 10% FBS and penicillin/streptomycin (Invitrogen). Recombinant human integrins $\alpha_v\beta_6$, $\alpha_v\beta_3$, $\alpha_v\beta_5$, $\alpha_5\beta_1$ were purchased from R&D Systems. All other chemicals were obtained from Fisher Scientific unless otherwise specified. Yeast media, growth and induction conditions and integrin binding buffer (IBB) are previously described (22).

Library Synthesis and Screening

The open reading frames encoding cystine knot peptides were generated by overlap-extension PCR using yeast optimized codons. Positions for randomization, denoted by "X" were constructed with NNB degenerate codons. PCR products were amplified using primers with overlap to the pCT yeast display plasmid upstream or downstream of the NheI and BamHI restriction sites, respectively. For each library, ~40 µg of DNA insert and 4 µg of linearized pCT vector were electroporated into the *S. cerevisiae* strain EBY100 by homologous recombination as previously described (26). For libraries L2 and L3, ~5–7×10$^6$ transformants per sub-library were combined for a total diversity of ~1×10$^7$ clones as estimated by serial dilution plating and colony counting. For libraries L2.1 and L3.1, ~2×10$^6$ transformants per sub-library were combined for a total diversity of ~4×10$^6$ clones.

For library screening, various concentrations of recombinant $\alpha_v\beta_6$ integrin were added to yeast suspended in IBB for various times at room temperature. Next, a 1:250 dilution of chicken anti-cMyc IgY antibody (Invitrogen) was added for 1 h at 4° C. The cells were washed with ice-cold IBB and incubated with a 1:25 dilution of fluorescein-conjugated anti-alpha-v integrin antibody (mAb 13C2, Millipore) and a 1:100 dilution of Alexa 555-conjugated goat anti-chicken IgG secondary antibody (Invitrogen) for 0.5 h at 4° C. Cells were washed in IBB and $\alpha_v\beta_6$ integrin binders were isolated using a Becton Dickinson FACS Aria III instrument. For the first round of sorting, ~2×10$^7$ yeast clones were screened with 100 nM $\alpha_v\beta_6$ integrin. To increase sort stringency, integrin concentrations were successively decreased to 1 nM in later sort rounds, and a diagonal sort gate was used to isolate yeast cells with enhanced integrin binding (FITC fluorescence) for a given protein expression level (Alexa 555 fluorescence). For the second diversification round, ~5×10$^6$ yeast clones were screened as described above with a final concentration of 300 pM $\alpha_v\beta_6$ integrin coupled with 3 days of washing in IBB at 37° C. Plasmid DNA was recovered by Zymoprep (Zymo Research), amplified in Max Efficiency DH5a *E. coli* cells (Invitrogen) and sequenced (Sequetech).

Electroporation was performed using cuvettes with a 2 mm gap. The electroporator was set to exponential decay mode, 540 millivolts and 25 microfarads. Approximately 1-2 ug vector DNA was combined with 10-20 ug of insert DNA per cuvette. Total transformed cells were then combined to achieve the reported library diversity.

Peptide Synthesis/Biosynthesis, Folding and Radiolabeling $S_O2$ and $R_O1$ were synthesized, folded and purified as previously described with a modification to the folding buffer, which included the addition of an equal volume of isopropanol and 800 mM guadinium hydrochloride (22). A20 was similarly prepared without folding. $R_O2$ and $E_O2$ were biosynthesized using *Pichia pastoris*. Peptides were conjugated through their N-terminus amine to DOTA-NHS and radiolabeled with $^{64}$CuCl$_2$ as previously described (19). The radiochemical purity was determined by HPLC to be >95%. The radiochemical yield was usually over 80%. The specific activity of the probe was ~500 Ci/mmol. Molecular masses were confirmed by MALDI-MS (ABI 5800).

The present peptides may be produced by recombinant DNA or may be synthesized in solid phase peptide synthesizer. They may further be capped at their N-termini by reaction with imaging labels, and, still further, may be synthesized with amino acid residues selected for additional crosslinking reactions. When the present peptides are produced by recombinant DNA, expression vectors encoding the selected peptide are transformed into a suitable host. The host should be selected to ensure proper peptide folding and disulfide bond formation as described above.

DOTA Conjugation

Approximately 1-2 mg of peptides were conjugated to ~2 mg DOTA-NHS in 1 mL DMF containing 20 uL triisopropylethylamine at room temperature for up to one hour. DOTA-peptides were purified by reverse phase HPLC.

Radiolabeling

Approximately 10 ug of peptide was incubated 2mCi $^{64}$CuCl$_2$ in 250 uL 100 mM sodium acetate buffer at 37° C. for at least one hour prior to purification by PD-10 column.

Biotinylation

Cystine knot peptides were coupled to PEO4-Biotin (Thermo) in DMF/2% DIEA for up to 1 h at room temperature with gentle rocking. The mixture was acidified with TFA/water and purified by RP-HPLC. A20 was coupled to AHA and Biotin using DIC/HOBt chemistry on an automated peptide synthesizer (CS Bio). Coupling time was approximately 3 hours per molecule.

Amino Acid Analysis

Amino acid analysis (AAA) was performed by Jay Gambee, AAA Service Laboratory in Damascus, Oreg. (http(colon slash slash) home.teleport.com/~aaaservs/index.html).

Biosynthesis of $R_O2$ and $E_O2$ $R_O2$ and $E_O2$ peptides were biosynthesized using the *Pichia* Expression Kit (Invitrogen K1710-01). The open reading frame encoding $R_O2$ or $E_O2$ and a hexahistidine tag (SEQ ID NO: 10) separated by a tobacco etch virus (TEV) protease cut site was inserted into a pPIC9K plasmid between EcoRI and NotI restriction sites. Plasmid (~10 ug) was linearized with SacI and electroporated into the GS115 *P. Pastoris* strain. The transformed yeast was recovered on RDB plates before being transferred to YPD plates with 4 mg/ml of geneticin. BMGY cultures with 4 mg/ml geneticin were inoculated with geneticin-resistant colonies and allowed to grow for 2-3 days. The cultures were induced in BMMY with 5% CAA and grown for 3-4 days with methanol concentration maintained at 1%. Peptide growth was monitored daily using RP-HPLC and molecular masses confirmed by matrix-assisted laser desorption/ionization time-of-flight mass spectrometry (MALDI-TOF MS). To purify the peptide, BMMY culture supernatant was passed through a Ni-NTA resin (Qiagen). The eluent containing the peptide-TEV-hexahistidine complex ("hexahistidine" disclosed as SEQ ID NO: 10) was lyophilized and resuspended in a buffered TEV protease solution to remove the hexahistidine tag (SEQ ID NO: 10). Cut protein was isolated by RP-HPLC, where protein without the tag had a shifted peak relative to protein with the tag.

Binding Affinity

Various concentrations of integrin $\alpha_v\beta_6$, $\alpha_v\beta_5$, $\alpha_v\beta_3$ and $\alpha_5\beta_1$ were incubated with $10^5$ yeast cells expressing $R_01$, $R_02$, $R_03$, $S_01$, $S_02$, $S_03$ or 2.5F in the presence of $10^6$ un-induced yeast cells as previously described (22, 27). See also United States Patent Application 20090257952 for details. Prior to flow cytometry and analysis, yeast cells were processed, stained, and washed as described above.

Flow Cytometric Analysis of Integrin $\alpha_v\beta_6$ Expression

BxPC-3, A431, U87MG, MDA-MB-435 and 293 cells were incubated with antibodies to separately detect the presence of the alpha-v and/or beta-6 integrin subunits. Binding of anti-alpha-v-FITC (Biolegend) and mouse anti-beta-6-IgG/human anti-mouse IgG (Invitrogen) to the cell surface integrin receptors was monitored by flow cytometry as per manufacturer's recommendation.

Protein and Cell Capture Assays

Neuravidin coated wells (Pierce) were saturated with biotinylated peptides A20, $R_01$, $S_02$ or 2.5F. 10 nM recombinant integrins or $10^5$ cells in IBB were added to wells at room temperature for 2 h. Wells were washed 3× with ice-cold IBB. Integrins were detected with mouse anti-alpha-v or anti-alpha-5 primary antibodies (Biolegend.com) and anti-mouse Alexa-488 (cellsignal.com). Cells were detected with crystal violet (22). Signals were quantified with a plate reader (Tecan). For competition binding assays, integrin $\alpha_v\beta_6$ or BxPC-3 cells were preincubated with $R_01$ or $S_02$ for 2 hours prior to introduction into A20 coated wells.

$^{64}$Cu-DOTA Peptide Stability

Aliquots of $^{64}$Cu-DOTA-peptide were incubated in an equal volume of mouse or human serum for up to 24 h. Samples were acidified with TFA and centrifuged to remove precipitants. In addition, $^{64}$Cu-DOTA-peptides were extracted from full mouse bladders 1.5-2 hour after injection. Soluble fractions were filtered with a Spin-X 0.2 μm filter (Corning) when necessary. All samples were analyzed by radio-HPLC on a Dionex $C_4$ column.

Cell Uptake

The assay was performed as previously described (28). Cells were suspended in IBB with $^{64}$Cu-DOTA labeled peptides at room temperature for 120 minutes. Cells were next washed three times with ice cold IBB and the pellet was collected by microcentrifugation. The bottom of the microcentrifuge tube was removed with canine nail clippers and placed into a scintillation tube where the radioactivity corresponding to the cell pellet was measured using a scintillation counter.

Tumor Models

Animal procedures were performed per protocol 11580 and 21637 (Stanford University Administrative Panels on Laboratory Animal Care). Female athymic nude mice, 4-6 weeks old (Charles River), were subcutaneously shoulder-injected with $10^7$ cells suspended in 100 μL PBS. Orthotopic tumors were generated with $10^6$ cells/20 uL Matrigel. Mice were anesthetized with isofluorane. A 5 mm incision was made just below the rib cage on the left side of the abdomen. The spleen and pancreas were gently coaxed out through the incision. One million cells in 20 uL matrigel were injected into the pancreas. The spleen and pancreas were then placed back into the abdomen, and the mouse was sutured. On a weekly basis, orthotopic tumors were monitored with ultrasound imaging using a dedicated small-animal high-resolution ultrasound scanner (40 MHz; Vevo 2100; VisualSonics, Toronto, Calif.). Mice were used for imaging/biodistribution studies when xenografts or orthotopic tumors reached ~10 mm or ~5 mm, respectively, in diameter.

MicroPET Imaging

Tumor-bearing mice (n=3 for each probe) were injected with ~50-100 μCi (~0.15 nmol) of probe via the tail vein and imaged with a microPET R4 rodent model scanner (Siemens) using 5 min static scans. Images were reconstructed by a two-dimensional ordered expectation maximum subset algorithm and calibrated as previously described (28). ROIs were drawn over the tumor on decay-corrected whole body images using ASIPro VM software (Siemens). ROIs were converted to counts/g/min, and % ID/g values were determined assuming a tissue density of 1 g/mL. No attenuation correction was performed.

Biodistribution Analysis

Anesthetized nude mice bearing xenograft/orthotopic tumors were injected with ~50-100 μCi (~0.15 nmol) of $^{64}$Cu-DOTA-peptides via tail vein, and euthanized after 1 h or 24 h. Tissues were removed, weighed and measured by scintillation counting (19, 29). Radiotracer uptake in tissues was reported as percent injected dose per gram (% ID/g) and represents the mean±standard deviation of experiments performed on three mice.

Statistical Analysis

All data are presented as the average value±the SD of at least 3 independent measurements. Statistical analysis for animal studies and binding studies were performed by two factor ANOVA without replication analysis using Microsoft Excel. Significance was assigned for p values of <0.05.

EXAMPLES

Example 1

Engineering $\alpha_v\beta_6$ Binders

Nine phage-display derived lead-motif (RTDLXXL (SEQ ID NO: 6)) containing sequences were engrafted into loop-1 of an acyclized cystine knot scaffold *Momordica cochinchinensis* Trypsin Inhibitor-II (MCoTI-II) from squash (14, 30, 31). These chimeric-binders are referred to as the "R-knots" ($R_0$) since MCoTI-II has high arginine content. Optimal loop-1 length and motif position were determined, and enabled design of libraries $X_3$RTDLXX$LX_3$ (SEQ ID NO: 11) and $X_4$RTDLXX$LX_3$ (SEQ ID NO: 12) (L2 and L3, Table 3), which were pooled and sorted by FACS. Flow cytomerty of clones G1-G9 was carried out with 100 nM integrin $\alpha_v\beta_6$ and 25 nM integrin $\alpha_v\beta_6$ (data not shown). Clones that demonstrated greatest binding were successively analyzed with lower concentrations of integrin $\alpha_v\beta_6$ to determine optimal motif position and loop length.

The $X_3$RTDLXX$LX_3$ (SEQ ID NO: 11) library dominated sort-round five (1 nM target). Frequent occurrence of arginine or lysine residues at certain loop positions suggested favorable binding interactions. Arginine was fixed at these positions in the second libraries (L2.1 and L3.1) to ensure a sole N-terminus amine for chemical labeling. The remaining loop positions were randomized (Table 3). The final sort-round was conducted in 300 pM target followed by 3 days of washing at 37° C. The top three most-represented binders (1, 2 and 3) were characterized.

TABLE 3

Process for Creating the Present Peptides

| Knottin | SEQ ID NO: | Loop-1 | Loop-2 | Loop-3 | Loop-4 | Loop-5 |
|---|---|---|---|---|---|---|
| R₀ | 33 | G C PKILKK---------- | C RRDSD | C PGA | C I C | RGNGY |
| G1 | 34 | G C --HPRTDLASLAKR-- | C RRDSD | C PGA | C I C | RGNGY |
| G2 | 35 | G C -GHPRTDLASLAKR-- | C RRDSD | C PGA | C I C | RGNGY |
| G3 | 36 | G C GGHPRTDLASLAKR-- | C RRDSD | C PGA | C I C | RGNGY |
| G4 | 37 | G C --HPRTDLASLAKRG- | C RRDSD | C PGA | C I C | RGNGY |
| G5 | 38 | G C -GHPRTDLASLAKRG- | C RRDSD | C PGA | C I C | RGNGY |
| G6 | 39 | G C GGHPRTDLASLAKRG- | C RRDSD | C PGA | C I C | RGNGY |
| G7 | 40 | G C --HPRTDLASLAKRGG | C RRDSD | C PGA | C I C | RGNGY |
| G8 | 41 | G C -GHPRTDLASLAKRGG | C RRDSD | C PGA | C I C | RGNGY |
| G9 | 42 | G C GGHPRTDLASLAKRGG | C RRDSD | C PGA | C I C | RGNGY |
| L2 | 43 | G C -XXXRTDLXXLXXX-- | C RRDSD | C PGA | C I C | RGNGY |
| L3 | 44 | G C XXXXRTDLXXLXXX-- | C RRDSD | C PGA | C I C | RGNGY |
| R₀1 | 2 | G C ILNMRTDLGTLLFR | C RRDSD | C PGA | C I C | RGNGY |
| L2.1 | 45 | G C RXXXRTDLXXLRXR-- | C RRDSD | C PGA | C I C | RGNGY |
| L3.1 | 46 | G C RXRXRTDLXXLRXR-- | C RRDSD | C PGA | C I C | RGNGY |
| R₀2 | 3 | G C RSLARTDLDHLRGR-- | C RRDSD | C PGA | C I C | RGNGY |
| R₀3 | 47 | G C RLVFRTDLDHLRGR-- | C RRDSD | C PGA | C I C | RGNGY |

Example 2

Scaffold Swapping and its Effects on Binding Affinity and Specificity

A novel $\alpha_v\beta_6$-binding activity, "2", was grafted into several arginine-rich scaffolds ($R_{0-3}$), glutamic acid-rich scaffolds ($E_{0-4}$) and serine-rich scaffolds ($S_{0-3}$). $\alpha_v\beta_6$-binding was determined by flow cytometry (Tables 4 and 5, FIG. 3B) to be comparable across scaffolds; maintenance of high-affinity binding to integrin $\alpha_v\beta_6$ indicates that engineered loops and knotted scaffolds can function independently and interchangeably. Novel integrin $\alpha_v\beta_6$ binding activities called "1", "2", and "3", were each tested in the context of both the $R_0$ and $S_0$ scaffolds for their ability to bind target. The $K_D$ of $R_0$1, $R_0$2, and $R_0$3 were measured to be 3.6±0.9 nM, 3.2±2.7 nM, 3.6±1.6 nM, respectively, by flow cytometry using soluble integrin $\alpha_v\beta_6$ (FIG. 1A). Interestingly, the $K_D$ of the $S_0$1, $S_0$2 was only slightly less at 6.5±2.0 nM and 6.0±0.1 nM, respectively, while the $K_D$ of $S_0$3 (3.1±0.5 nM) matched that of its parent (FIG. 1B). These results suggest that the knotted structure is tightly maintained in engineered $R_0$ and $S_0$ binders, so that novel activities can be trans-grafted into other wild type or rationally-designed knots without notable loss of potency (FIG. 3B). $\alpha_v\beta_6$ binding activity "2", RSLARTDLDHLRGR (SEQ ID NO: 7), was grafted into several natural and modified cystine knot scaffolds. Their relative binding affinities for 10 nM integrin $\alpha_v\beta_6$ were compared to $R_O2$ set equal to 1 (FIG. 3B). Cross-reactivity of peptides used throughout these studies to other integrins was also tested. Peptides demonstrate very low binding to integrins $\alpha_v\beta_3$, $\alpha_v\beta_5$ and $\alpha_v\beta_1$ (FIG. 1C). Scrambled versions of the peptides contain the sequence RDTLXXL (SEQ ID NO: 9) where TD has been scrambled to DT. Scrambled peptides did not bind integrin $\alpha_v\beta_6$ (FIG. 3A).

petition between peptides for a specific target-binding site (FIG. 2B). A20, $R_O1$ and $S_O2$ also captured cells that express native integrin $\alpha_v\beta_6$ (FIG. 2C). Flow cytometry showed all tested cell lines (BxPC-3, A431, U87MG, MDA-MB-435) but the 293 cells express integrin $\alpha_v\beta_6$. Peptides $R_O1$ and $S_O2$ blocked adhesion of BxPC-3 cells onto A20 coated wells confirming specific binding between peptides and functionally-active integrins expressed on cellular surfaces (FIG. 2D).

TABLE 4

Primary Structure of Naturally Occurring Trypsin Inhibitor Cystine Knot Peptides

| Knottin | SEQ ID NO: | | Loop-1 | Loop-2 | | Loop-3 | | Loop-4 + Loop-5 |
|---|---|---|---|---|---|---|---|---|
| MCoTI-II | 13 | - - - - V | C PKILKK C | RRDSD | C | PGA | C | ICRGN-GY |
| MCO-TI-I | 14 | - - - - V | C PKILQR C | RRDSD | C | PGA | C | ICRGN-GY |
| MCTI-I | 15 | - - ERR | C PRILKQ C | KRDSD | C | PGE | C | ICMAH-GF |
| BDTI-II | 16 | - - - RG | C PRILMR C | KRDSD | C | LAG | C | VCQKN-GY |
| MRTI-I | 17 | - - - GI | C PRILME C | KRDSD | C | LAQ | C | VCKR-QGY |
| MCTI-II | 18 | - - - RI | C PRIWME C | KRDSD | C | MAQ | C | ICV-DGH |
| CMTI-III | 19 | HEERV | C PRILMK C | KKDSD | C | LAE | C | VCLE-HGY |
| CMTI-I | 20 | - - - RV | C PRILME C | KKDSD | C | LAE | C | VCLE - HGY |
| CMTI-IV | 21 | HEERG | C PRILMK C | KKDSD | C | LAE | C | VCLE-HGY |
| CPTI-II | 22 | HEERV | C PRILME C | KKDSD | C | LAE | C | ICLE-HGY |
| EETI-II | 23 | - - - - G | C PRILMR C | KQDSD | C | LAG | C | VCGPN-GF |
| MCTI-III | 24 | - - ERG | C PRILKQ C | KQDSD | C | PGE | C | ICMAH-GF |
| CMCTI-III | 25 | - -QRM | C PKILMK C | KQDSD | C | LLD | C | VCLKE-GF |
| CMCTI-I | 26 | - - - - M | C PKILMK C | KQDSD | C | LLD | C | VCLKE-GF |
| CSTI-IV | 27 | - - -MM | C PRILMK C | KHDSD | C | LPG | C | VCLEHIEY |
| CSTI-IIB | 28 | - - - MV | C PRILMK C | KHDSD | C | LLD | C | VCLEDIGY |
| LCTI-IV | 29 | - - - - I | C PRILMP C | SSDSD | C | LAE | C | ICLE-NGF |
| LCTI-III | 30 | - - - RI | C PRILME C | SSDSD | C | LAE | C | ICLE-NGF |
| LCTI-II | 31 | - - - RI | C PRILME C | SSDSD | C | LAE | C | ICLEQGF |
| LCTI-I | 32 | - - - RI | C PRILME C | SSDSD | C | LAE | C | ICLE-QGF |

Example 3

Protein and Cell Capture Assays

Biotinylated peptides A20, $R_O1$, $S_O2$ and 2.5F were immobilized onto neuravidin coated plates. All four peptides captured recombinant integrin $\alpha_v\beta_6$, but only knottin 2.5F captured integrins $\alpha_v\beta_3$, $\alpha_v\beta_5$ and $\alpha_5\beta_1$. Engineered binders show different levels of specificity for their targets (FIG. 2A). Biotinylated A20, precoated onto microwell plates, engaged in competitive binding with soluble $R_O1$ or $S_O2$ for recombinant integrin $\alpha_v\beta_6$. Dose dependent inhibition indicated com-

[64]Cu-DOTA-labeled peptides also demonstrated binding to target expressing cells and not to 293 negative controls (FIG. 5).

Cell uptake assays were performed with $^{64}$Cu-DOTA labeled versions of the engineered knots and the positive control, A20. $^{64}$Cu-DOTA-A20 rapidly associated with A431 cells and BxPC-3 pancreatic cancer cells. New binders, $^{64}$Cu-DOTA-labeled versions of $R_O1$ and $R_O2$ and to a lesser extent $E_O2$ and $S_O2$ bind these positive cell lines shown by the black bar and white bar of FIG. 5. These results suggest that cellular association of radiotracers correlates to overexpression of integrin $\alpha_v\beta_6$. For each of the radiotracers, substantially less

Example 4

Scaffold Reformatting: Serum and Metabolic Stability of Peptides

Figures 4A, 4B:
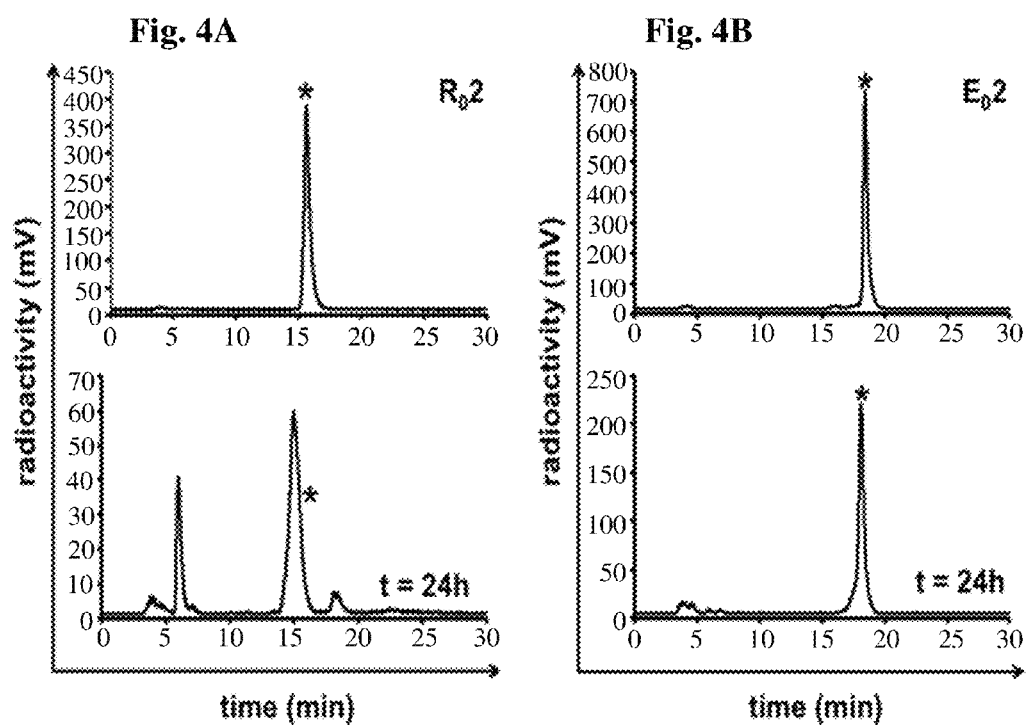
FIG. 4A is a graph showing $^{64}$Cu-DOTA-labeled $R_o2$ serum stability.
FIG. 4B is a graph showing $^{64}$Cu-DOTA-$E_o2$ serum stability.
Figure 7:
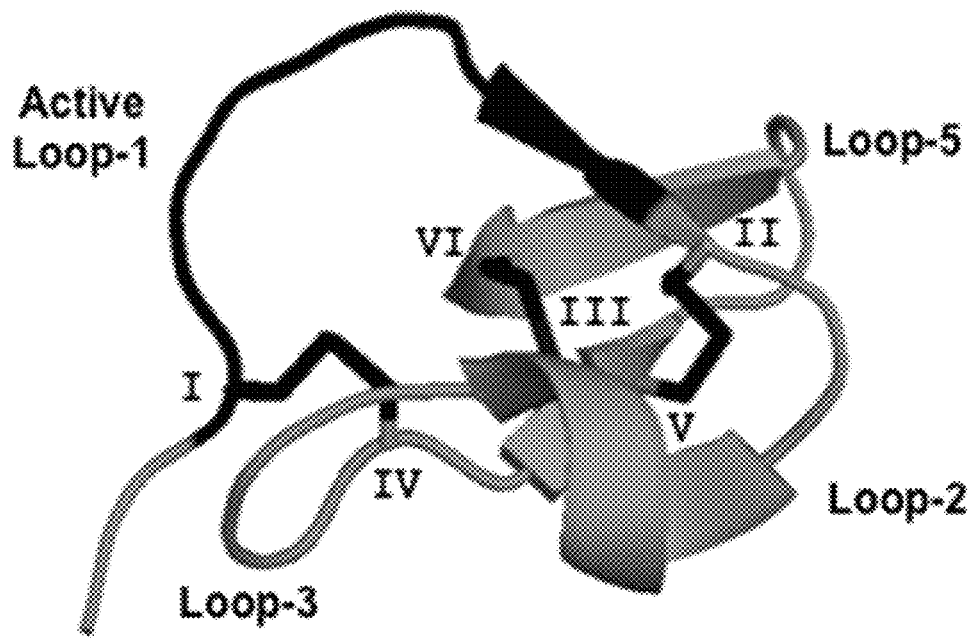
FIG. 7 is a three dimensional drawing showing the structure of McoTI-II (R0, Protein Data Bank accession 2IT8) and its active loop (black) are stabilized by three knotted disulfide bonds (black) formed by six cystine residues (I-VI).

Most wild-type and engineered knots resist degradation/denaturation in physiological media such as serum and urine (19, 23, 29). However, loop engineering can compromise stability. For example, $R_O2$ was ~80% degraded during 24 h serum incubation (FIG. 4A). Comparatively, $^{64}$Cu-DOTA-labeled $R_O1$ demonstrated much greater stability; approximately 20% degradation occurred during 24 h serum incubation. These two peptides share identical primary sequences in loops 2 through 5 of their structural frames (Tables 4 and 5, FIG. 7).

The primary sequence of the wild type trypsin inhibitor cystine knot framework ($R_O$) includes six cystine residues with disulfide connectivity (six individual columns) and five loops. Grafts one to nine (G1-G9) each contain the RTDLXX L motif (SEQ ID NO: 6) (underlined). Libraries L2 and L3 were derived from highest affinity grafts, G2 and G3. High-affinity binder $R_O1$ emerged after 5 sort rounds. Libraries, L2.1 and L3.1, fixed arginine residues to prevent the occurrence of lysine at those positions. Binders $R_O2$ and $R_O3$ emerged from sorting.

TABLE 5

Engineering Process of the Present Peptides

| Knottin | SEQ ID NO: | Loop-1 | Loop-2 | Loop-3 | 4 | Loop-5 |
|---|---|---|---|---|---|---|
| $R_O2$ | 3 | G C RSLARTDLDHC | RRDSD | C PGA | C I C | RGNGY C LRGR |
| $R_12$ | 48 | G C RSLARTDLDHC | RRDRD | C PGA | C I C | RGNGY C LRGR |
| $R_22$ | 49 | G C RSLARTDLDHC | RRDSD | C RGA | C I C | RGNGY C LRGR |
| $R_32$ | 50 | G C RSLARTDLDHC | RRDRD | C RGA | C I C | RGNGY C LRGR |
| $E_12$ | 51 | G C RSLARTDLDHC | RRDSD | C PGA | C I C | EGNGY C LRGR |
| $E_22$ | 52 | G C RSLARTDLDHC | RRDSD | C PGA | C I C | RGNGY C LRGR |
| $E_32$ | 53 | G C RSLARTDLDHC | REDSD | C PGA | C I C | RGNGY C LRGR |
| $E_42$ | 54 | G C RSLARTDLDHC | EEDSD | C PGA | C I C | EGNGY C LRGR |
| $E_O2$ | 55 | G C RSLARTDLDHC | EEDSD | C LAE | C I C | EGNGY C LRGR |
| $S_O2$ | 56 | G C RSLARTDLDHC | RRDSD | C LAE | C I C | RGNGY C LRGR |
| $S_12$ | 57 | G C RSLARTDLDHC | RRDSD | C SAE | C I C | RGNGY C LRGR |
| $S_22$ | 58 | G C RSLARTDLDHC | RRDSD | C LAE | C I C | RGNGY C LRGR |
| $S_32$ | 59 | G C RSLARTDLDHC | RRDSD | C SAE | C I C | RGNGY C LRGR |

The arginine-rich ($R_O$), glutamic acid-rich ($E_O$) and serine-rich ($S_O$) frameworks show the number and positions of amino acids (underlined gray-back letters) that were substituted. The names of peptides that were fully characterized in vitro and validated in vivo are shown in gray-back letters.

Figure 4C:
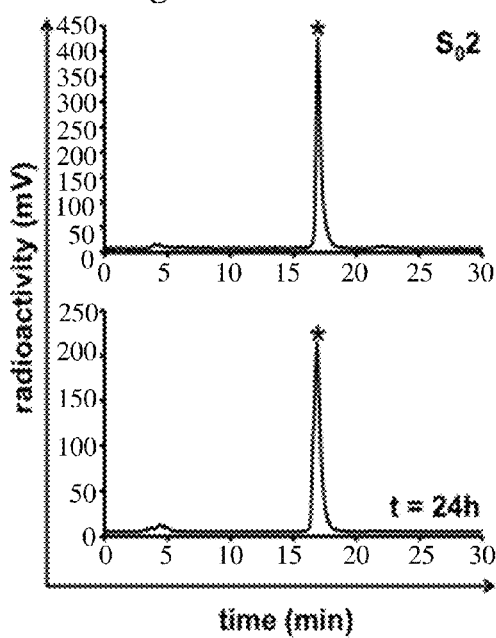
FIG. 4C is a graph illustrating $^{64}$Cu-DOTA-$S_o2$ serum stability.
Figure 4D:
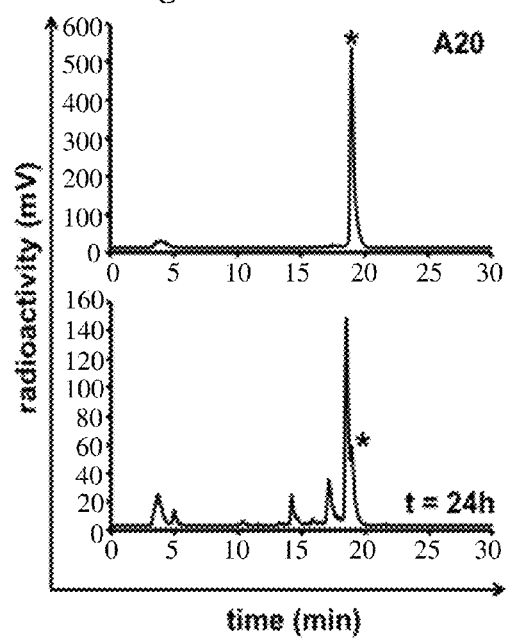
FIG. 4D is a graph showing the control $^{64}$Cu-DOTA-A20 in serum.

In contrast, $^{64}$Cu-DOTA-$S_O2$ and -$E_O2$ demonstrated exceptionally high (>95%) stability during 24 h serum incubation (FIG. 4B, 4C). For completeness, the linear control $^{64}$Cu-DOTA-A20 was >90% degraded after 24 h incubation in serum (FIG. 4D). Urine samples drawn from mice 1.5-2 h after injection showed ~20% degradation of $^{64}$Cu-DOTA-$R_O1$ and <5% degradation of $^{64}$Cu-DOTA $S_O2$, the current lead translational candidates. $^{64}$Cu-DOTA-$R_O1$ and $^{64}$Cu-DOTA-$S_O2$ were recovered from mouse urine 1.5-2 h post injection and analyzed by radio HPLC. The intact radiotracer was detected as a single main peak. Metabolites were indicated by any deviation from the main peak. In the case of $^{64}$Cu-DOTA-$R_O1$, a metabolite elutes immediately before the main peak. In the case of $^{64}$Cu-DOTA-$S_O2$, a small amount of free $^{64}$Cu elutes with the dead volume at approximately 4 to 5 minutes. It was suspected there was a negligible amount of decoupling of $^{64}$Cu from the DOTA chelator. These results demonstrate that non-binding portions of peptide scaffolds may be used to increase in vivo stability.

Example 5

MicroPET Imaging and Biodistribution

Radio-labeled versions of knots were evaluated by PET in mice bearing integrin $\alpha_v\beta_6$-expressing BxPC-3 (pancreatic cancer) or A431 (epidermoid cancer) xenografts, and $\alpha_v\beta_6$-negative 293 tumors. Mice were injected with ~75 uCi of $^{64}$Cu-DOTA labeled peptides. $R_O2$, $E_O2$, $S_O2$, $R_O1$ and the positive control A20, rapidly accumulated in $\alpha_v\beta_6$-positive A431 tumors and generated excellent tumor-to-muscle contrast ratios of 6-11 at 1 h post injection (p.i.). Absolute uptake in A431 tumors was highest for the two $R_O$-based binders $R_O1$ (~5% ID/g) and $R_O2$ (~4% ID/g) compared to $E_O2$ (~1.5% ID/g), $S_O2$ (~2% ID/g) and A20 (~2% ID/g) at 1 h p.i.

PET studies of BxPC-3 pancreatic xenografts confirmed these results. Importantly, significantly less radiotracer accumulated in $\alpha_v\beta_6$-negative 293 xenografts. Comparatively, tumor uptake of $R_O2$, measured 4.3±0.7% ID/g in BxPC-3 xenografts compared to 1.3±0.1% ID/g in 293 xenografts. $S_O2$ and $R_O1$ corroborated these results. Collectively, these results show that the $\alpha_v\beta_6$-specific probes selectively bind $\alpha_v\beta_6$-positive (T+) tumors (A431 and BxPC-3) and do not accumulate in the $\alpha_v\beta_6$-negative (T−) 293 tumors. Unfortunately, conclusive identification of orthotopic BxPC-3 tumors by PET remained elusive.

Biodistribution analysis of $R_O1$ and $S_O2$ in BxPC-3 xenograft tumors showed 4.13±1.01 and 1.80±0.50% ID/g 1 h p.i. These data closely matched corresponding PET data (Table 2A). Importantly, $S_O2$ effectively accumulated in BxPC-3 orthotopic tumors (1.85±0.11% ID/g, 1 h p.i.) compared to normal pancreas (~0.2-0.3% ID/g, 1 h p.i., Table 1). However, substantial amounts of $S_O2$ accumulated in liver, stomach, intestines and kidneys as measured by biodistribution analysis and seen by PET imaging (Tables 2A, 2B).

$R_O2$ and $R_O1$ accumulated to greater levels in A431 tumors compared to $E_O2$ and $S_O2$. However, these arginine-rich binders cleared slowest from surrounding muscle tissue. Biodistribution analysis indicated ~0.6% ID/g muscle at 1 h for the $R_O2$, while approximately half (~0.3% ID/g) was observed for $E_O2$ and $S_O2$ (Tables 6A, 6B). Therefore, tumor-to-muscle contrast was comparable for each of the engineered knots.

Biodistribution of $^{64}$Cu-DOTA-labeled peptides in αvβ$_6$-positive A431 xenografts
Data are presented as mean % ID/g ± SD

| | $^{64}$Cu-DOTA-R$_0$2 | | $^{64}$Cu-DOTA-E$_0$2 | | $^{64}$Cu-DOTA-S$_0$2 | | $^{64}$Cu-DOTA-R$_0$1 | |
|---|---|---|---|---|---|---|---|---|
| Tissue | 1 h | 24 h | 1 h | 24 h | 1 h | 24 h | 1 h | 24 h |
| Tumor | 4.43 ± 0.26 | 5.18 ± 0.51 | 1.8 ± 0.25 | 1.70 ± 0.26 | 2.10 ± 0.45 | 2.07 ± 0.49 | 4.65 ± 0.94 | 3.25 ± 0.88 |
| Muscle | 0.62 ± 0.06 | 0.54 ± 0.14 | 0.27 ± 0.29 | 0.24 ± 0.07 | 0.23 ± 0.09 | 0.23 ± 0.03 | 0.53 ± 0.06 | 0.39 ± 0.02 |
| Blood | 0.43 ± 0.04 | 0.63 ± 0.16 | 0.28 ± 0.10 | 0.24 ± 0.03 | 0.38 ± 0.17 | 0.31 ± 0.15 | 0.50 ± 0.17 | 0.43 ± 0.01 |
| Heart | 0.54 ± 0.14 | 1.64 ± 0.59 | 0.27 ± 0.04 | 0.44 ± 0.11 | 0.40 ± 0.17 | 0.29 ± 0.04 | 0.57 ± 0.22 | 0.50 ± 0.14 |
| Kidney | 115.8 ± 11.9 | 50.41 ± 11.33 | 115.6 ± 23.9 | 40.65 ± 5.05 | 28.78 ± 9.80 | 13.69 ± 0.89 | 79.70 ± 15.7 | 42.74 ± 0.14 |
| Liver | 3.18 ± 0.16 | 5.34 ± 2.37 | 2.41 ± 0.35 | 3.50 ± 0.83 | 4.36 ± 1.15 | 5.37 ± 0.13 | 3.05 ± 0.60 | 3.26 ± 0.26 |
| Lung | 2.52 ± 0.53 | 3.37 ± 1.37 | 0.93 ± 0.12 | 1.25 ± 0.56 | 1.65 ± 0.86 | 1.48 ± 0.10 | 2.31 ± 1.16 | 1.75 ± 0.31 |
| Spleen | 0.68 ± 0.21 | 1.53 ± 0.28 | 0.41 ± 0.07 | 0.42 ± 0.20 | 0.65 ± 0.48 | 0.54 ± 0.15 | 0.93 ± 0.43 | 0.87 ± 0.35 |
| Pancreas | 0.52 ± 0.04 | 1.12 ± 0.13 | 0.19 ± 0.05 | 0.41 ± 0.16 | 0.34 ± 0.02 | 0.44 ± 0.11 | 0.49 ± 0.11 | 0.44 ± 0.07 |
| Stomach | 3.58 ± 0.58 | 5.34 ± 2.07 | 0.61 ± 0.13 | 1.08 ± 0.25 | 1.86 ± 0.57 | 1.22 ± 0.30 | 2.08 ± 1.10 | 1.09 ± 0.14 |
| Intestine | 2.48 ± 0.30 | 2.83 ± 0.90 | 0.56 ± 0.11 | 1.15 ± 0.18 | 1.78 ± 0.88 | 0.91 ± 0.13 | 1.86 ± 0.64 | 0.88 ± 0.79 |
| Brain | 0.12 ± 0.02 | 0.24 ± 0.06 | 0.07 ± 0.03 | 0.19 ± 0.09 | 0.10 ± 0.06 | 0.14 ± 0.03 | 0.14 ± 0.05 | 0.18 ± 0.08 |
| Bone | 0.23 ± 0.10 | 0.67 ± 0.58 | 0.20 ± 0.05 | 0.25 ± 0.12 | 0.30 ± 0.20 | 0.40 ± 0.12 | 0.50 ± 0.25 | 0.47 ± 0.13 |
| Skin | 1.15 ± 0.32 | 0.81 ± 0.15 | 0.52 ± 0.15 | 0.35 ± 0.09 | 1.00 ± 0.44 | 0.82 ± 0.15 | 1.47 ± 0.32 | 0.81 ± 0.19 |

TABLE 6B

Tumor-to-Normal Tissue Ratios

| | $^{64}$Cu-DOTA-R$_0$2 | | $^{64}$Cu-DOTA-E$_0$2 | | $^{64}$Cu-DOTA-S$_0$2 | | $^{64}$Cu-DOTA-R$_0$1 | |
|---|---|---|---|---|---|---|---|---|
| Ratio | 1 h | 24 h | 1 h | 24 h | 1 h | 24 h | 1 h | 24 h |
| T/Muscle | 7.20 ± 0.36 | 5.18 ± 0.51 | 7.06 ± 1.81 | 7.53 ± 1.52 | 9.38 ± 1.70 | 9.20 ± 1.90 | 8.74 ± 1.48 | 8.17 ± 1.93 |
| T/Blood | 10.31 ± 0.76 | 8.45 ± 1.41 | 6.69 ± 1.71 | 7.32 ± 1.99 | 6.11 ± 2.11 | 7.53 ± 3.34 | 9.67 ± 2.16 | 7.49 ± 1.90 |
| T/Liver | 1.39 ± 0.06 | 0.88 ± 0.27 | 0.77 ± 0.22 | 0.51 ± 0.17 | 0.49 ± 0.05 | 0.39 ± 0.10 | 1.55 ± 0.32 | 1.00 ± 0.28 |
| T/Lung | 1.78 ± 0.19 | 1.67 ± 0.48 | 1.98 ± 0.51 | 1.64 ± 0.95 | 1.54 ± 0.77 | 1.42 ± 0.43 | 2.34 ± 1.03 | 1.95 ± 0.88 |
| T/Spleen | 7.00 ± 2.43 | 3.44 ± 0.45 | 4.48 ± 1.23 | 4.76 ± 2.24 | 5.11 ± 4.08 | 4.30 ± 2.53 | 5.49 ± 3.23 | 3.92 ± 0.81 |
| T/Pancreas | 8.56 ± 1.10 | 4.68 ± 0.91 | 9.85 ± 2.12 | 4.61 ± 1.94 | 7.74 ± 4.16 | 5.09 ± 2.37 | 9.77 ± 2.40 | 7.57 ± 2.41 |
| T/Kidneys | 0.04 ± 0.01 | 0.11 ± 0.02 | 0.02 ± 0.00 | 0.04 ± 0.00 | 0.08 ± 0.01 | 0.15 ± 0.04 | 0.06 ± 0.10 | 0.08 ± 0.03 |

Renal retention varied by binding activity and scaffold. $R_0$1 ranged from ~45% ID/g (1 h) to ~20% ID/g (24 h), whereas $R_0$2 ranged from ~75% ID/g (1 h) to ~28% ID/g (24 h). This difference is attributed to the higher arginine content of activity "2". However, transfer of activity "2" to the carboxyl-rich scaffold ($E_0$2) did not decrease kidney signal (~72% ID/g (1 h) and ~16% ID/g (24 h)). These results suggest that in addition to arginine residues, the kidneys also actively retain carboxyl-containing residues. Importantly, when the "2" activity was tested in the $S_0$ scaffold ($S_0$2), significantly lower renal retention was measured (~18% ID/g (1 h) and ~7% ID/g (24 h)). The large differences in renal uptake suggest that scaffold pharmacokinetics may be optimized to evade renal reuptake and allow a binder to pass freely into the bladder. Arginine is one of the most versatile amino acids in animal cells, serving as a precursor for the synthesis of proteins, nitric oxide, urea, polyamines, proline, glutamate, creatine and agmatine (32). Therefore, arginine recycling by the kidneys is beneficial to the organism. By substituting pharmacokinetically favorable amino acids in the diversity-tolerant cystine knot framework, non-specific uptake by off-target tissues may be reduced.

Example 6

$^{18}$F-Labeled Ro1 and So2 for PET Imaging of Integrin α$_v$β$_6$ Tumors

In this example, $R_0$1 and $S_0$2 were labeled with N-succinimidyl-4-$^{18}$F-fluorobenzoate at 93% ($^{18}$F-FB-$R_0$1) and 99% ($^{18}$F-FB-$S_0$2) purity. $^{18}$F-FB-$R_0$1 and $^{18}$F-FB-$S_0$2 were 87% and 94% stable in human serum at 37° for 2 h. $^{18}$F-FB-peptides (2-3 MBq) were injected via tail-vein into nude mice, and exhibited 2.3±0.6% ID/g and 1.3±0.4% ID/g, respectively, in BxPC3 xenografted tumors at 0.5 h (n=4-5). (BxPC3 is a known pancreatic cancer cell line.) Target specificity was confirmed by low tumor uptake in integrin α$_v$β$_6$-negative 293 tumors (1.4±0.6 and 0.5±0.2% ID/g for $^{18}$F-FB-$R_0$1 and $^{18}$F-FB-$S_0$2, both P<0.05; n=3-4) and low muscle uptake (3.1±1.0 and 2.7±0.4 tumor:muscle for $^{18}$F-FB-$R_0$1 and $^{18}$F-FB-$S_0$2). MicroPET data were corroborated by ex vivo gamma counting of dissected tissues, which demonstrated low uptake in non-target tissues with only modest kidney uptake (9.2±3.3 and 1.9±1.2% ID/g at 2 h for $^{18}$F-FB-$R_0$1 and $^{18}$F-FB-$S_0$2; n=8). Uptake in healthy pancreas was low (0.3±0.1% for $^{18}$F-FB-$R_0$1 and 0.03±0.01% for $^{18}$F-FB-$S_0$2; n=8). Thus, these cystine knot peptide tracers, in particular $^{18}$F-FB-$R_0$1, show translational promise for molecular imaging of integrin α$_v$β$_6$ overexpression in pancreatic and other cancers.

$^{64}$Cu labeling of these peptides via a DOTA chelator enabled effective microPET of mice bearing BxPC3 pancreatic adenocarcinoma and A431 epidermoid carcinoma xenografted tumors (39). Tumor uptake with an arginine-rich scaffold was 4.7±0.9% ID/g at 1 h with 8.7±1.5 tumor:muscle contrast, and the peptide was 80% stable in serum for 24 h. A serine-rich cystine knot peptide had 2.1±0.5% ID/g tumor, 9.4±1.7 tumor:muscle, and >95% serum stability at 24 h. The rapid tumor localization and background clearance of these small peptides enables imaging as early as 1 h post-injection. Thus, $^{18}$F is a preferred radioisotope for clinical translation of these agents because of its greater positron yield and faster decay (for reduced radiation exposure). 18F-FB-R01 and 18F-FB-S02 were 87% and 94% stable in human serum at 37° C. for 2 h.

The two $^{18}$F-labeled integrin $\alpha_v\beta_6$-targeted cystine knot peptides demonstrated microPET imaging of pancreatic adenocarcinoma xenografted tumors in mice. Pancreatic cancer is of particular interest because of the critical need for a molecular imaging agent for early detection as 80% of pancreatic cancers have local advancement or metastasis at time of presentation (40).

Peptide Synthesis and Radiochemistry

Peptides $R_01$ and $S_02$ were synthesized using standard Fmoc chemistry, folded, and purified by RP-HPLC as described (39). Protein mass was verified by matrix-assisted laser desorption/ionization—time of flight—mass spectrometry (MALDI-TOF-MS). The amine-reactive radiolabeling agent N-succinimidyl-4-$^{18}$F-fluorobenzoate ($^{18}$F-SFB) was synthesized using Tracerlab FX-FN in a slightly modified version of the previously published protocol. Three mg of 4-(ethoxycarbonyl)-N,N,N-trimethylbenzenaminium triflate precursor was reacted with 6.8 GBq of dried $^{18}$F at 90° for 10 min. $^{18}$F-4-fluorobenzoic acid was prepared by reaction with 50 μmoles of tetrapropylammonium hydroxide at 120° for 3 min. Acetonitrile was added and evaporated to remove residual water. The reaction mixture was added to 10 mg of O-(N-succinimidyl)-1,1,3,3-tetramethyluronium tetrafluoroborate (TSTU) and heated at 90° for 5 min. to produce $^{18}$F-SFB. Eight mL of 5% acetic acid were added and used to transfer the crude reaction mixture to a dilution flask with 12 mL of water. The mixture was passed through a C18 Plus cartridge, washed with 10 mL of 10% acetonitrile in water, and eluted with 3 mL acetonitrile. $^{18}$F-SFB was dried under vacuum at 60°, resuspended in 50 μL DMSO, and reacted with about 300 μg of folded peptide in 300 μL of 0.1 M sodium phosphate, pH 7.5 at 50° for 45 min. $^{18}$F-FB-peptide was purified by semi-preparative RP-HPLC on a C18 column using a gradient of 25-65% over 35 min. for $R_01$ and 22.5-27.5% over 35 min. for $S_02$. Solvent was removed by rotary evaporation, and peptide was prepared in phosphate-buffered saline.

Serum Stability $^{18}$F-FB-peptide in PBS was mixed with an equal volume of human serum and incubated at 37°, 300 rpm for 2 h. Trifluoroacetic acid was added and the soluble fraction was clarified with a 0.22 μm filter. The sample was separated by RP-HPLC on a C18 column with a gradient of 5-85% acetonitrile in water (both with 0.1% trifluoroacetic acid) from five to 35 minutes and analyzed with a gamma ray detector.

Small Animal Imaging and Tissue Biodistribution

Animal experiments were conducted in accordance with federal and institutional regulations under a protocol approved by the Stanford University Institutional Animal Care and Use Committee. Ten million integrin $\alpha_v\beta_6$-positive BxPC3 pancreatic adenocarcinoma cells or integrin $\alpha_v\beta_6$-negative HEK-293 cells were subcutaneously injected into the shoulder of six-week old female nu/nu mice. Xenografted tumors were grown to ten millimeter diameter. Mice were anesthetized with isoflurane and injected via the tail vain with 2-3 MBq of $^{18}$F-FB-peptide. A rodent R4 microPET (Siemens) was used to acquire five-minute static scans at 0.5, 1, and 2 h post-injection or a 10-minute dynamic scan. Tumor, kidney, liver, and hind leg muscle signals were quantified with AsiProVM for static scans and AMIDE (41) for dynamic scans. Following the 2 h static scan, mice were euthanized, tissues were collected and weighed, and activity was measured with a gamma ray counter. Decay-corrected activity per mass of tissue was calculated. All data are presented as mean±standard deviation. Statistical significance was tested using the two-tailed Student t-test with a threshold of P<0.05.

Results of Peptide Synthesis and Radiochemistry

Figure 6:
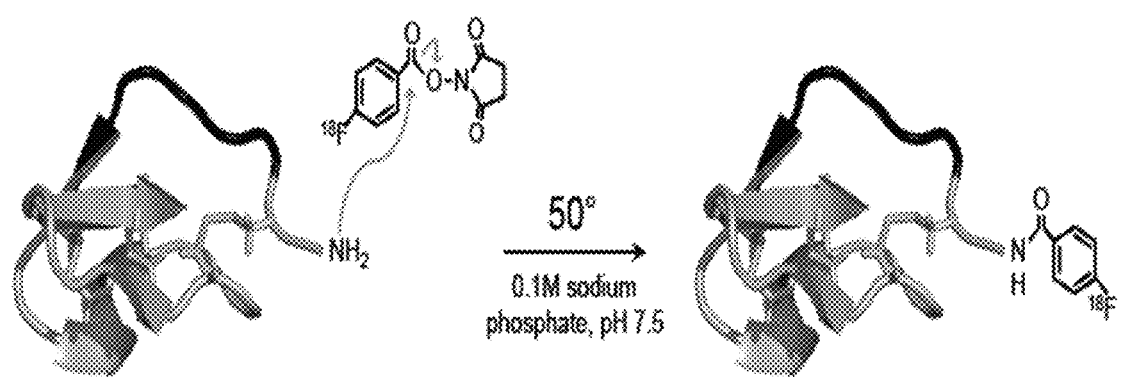
FIG. 6 is a schematic drawing showing the cystine knot peptides $R_o1$ and $S_o2$, which contain three disulfide bonds, an active binding loop, and a sole primary amine at the N-terminus.

Peptides $R_01$ and $S_02$ (FIG. 6) were synthesized using standard Fmoc chemistry. Mass was verified by MALDI-TOF-MS: $R_01$ 3908.7 Da (3908.8 Da expected), $S_02$ 3875.5 Da (3874.7 Da expected). Peptides were folded and purified by RP-HPLC. Removal of six hydrogens during oxidation was verified by MALDI-TOF-MS: $R_01$ 3902.8 Da, $S_02$ 3868.4 Da. $^{18}$F-SFB was synthesized in 1 h with a 40% decay-corrected yield. Three hundred μg of folded peptide was reacted with 740 MBq of $^{18}$F-SFB in 0.1 M sodium phosphate, pH 7.5 at 50° for 45 min. $^{18}$F-FB-peptide was purified by RP-HPLC. Solvent was removed by rotary evaporation and peptide was resuspended in PBS. $^{18}$F-FB-$R_01$ and $^{18}$F-FB-$S_02$ were 93% and >99% pure as measured by analytical RP-HPLC. Decay corrected yield from $^{18}$F-SFB was xxx for $^{18}$F-FB-$R_01$ and 5% for $^{18}$F-FB-$S_02$. $^{18}$F-FB-$R_01$ and $^{18}$F-FB-$S_02$ were 87% and 94% stable for 2 h at 37° in human serum.

MicroPET Imaging

The radiolabeled peptides were used for microPET imaging of mice bearing BxPC3 pancreatic adenocarcinoma xenografted tumors. Nude mice were inoculated with $10^7$ BxPC3 cells, which express integrin $\alpha_v\beta_6$. When ten millimeter tumors formed, mice were injected with 2-3 MBq of $^{18}$F-FB-peptide, and microPET was performed. Tumor was clearly visualized relative to background as early as 0.5 h post-injection for both peptides. As was the case for the $^{64}$Cu-DOTA versions of the peptides, $^{18}$F-FB-$R_01$ exhibits greater tumor uptake (2.3±0.6% ID/g) than $^{18}$F-FB-$S_02$ (1.3±0.4%), and both have comparable tumor:muscle ratios: 3.1±1.0 and 2.9±0.4 at 0.5 and 1 h for $^{18}$F-FB-$R_01$; 2.7±0.4 and 4.0±1.0 at 0.5 and 1 h for $^{18}$F-FB-$S_02$.

To further demonstrate integrin $\alpha_v\beta_6$ specificity, microPET experiments were performed with xenografted tumors of 293 cells, which do not express integrin $\alpha_v\beta_6$ (39). $^{18}$F-FB-$R_01$ exhibits 1.4±0.6% ID/g tumor signal, which is significantly less (p=0.04) than BxPC3 xenografts. Likewise, $^{18}$F-FB-$S_02$ has lower uptake into 293 tumors than BxPC3 tumors (0.5±0.2%, p=0.02).

Both tracers exhibit modest kidney uptake (27±4% for $^{18}$F-FB-$R_01$ and 18±6% for $^{18}$F-FB-$S_02$) and low liver uptake (2.0±0.7% for $^{18}$F-FB-$R_01$ and 0.9±0.3% for $^{18}$F-FB-$S_02$).

Dynamic PET demonstrates the rapid distribution of the peptides, as tumor targeting is 95% complete within five minutes for both peptides. The rapid tumor signal stabilization is consistent with the rapid clearance of both peptides: analysis of the radioactivity in the heart reveals blood clearance half-times of 1.6 min. for $^{18}$F-FB-$R_01$ and 1.8 min. for $^{18}$F-FB-$S_02$.

Tissue Biodistribution

Further tissue biodistribution was obtained via activity measurements of resected tissues from mice euthanized at 2 h post-injection. These data closely match the microPET results for tumor, muscle, kidney, and liver. Tumor:blood ratios of 6.0±1.1 and 3.1±0.8 were achieved for $^{18}$F-FB-$R_01$ and $^{18}$F-FB-$S_02$, respectively. Very low non-target uptake is observed in other tissues aside from moderate uptake in the lungs (2.9±1.2%, n=8) and stomach (1.6±0.4%, n=8) for $^{18}$F-FB-$R_01$.

The engineered $R_01$ and $S_02$ peptides were validated as targeting domains for molecular PET imaging of integrin $\alpha_v\beta_6$ using $^{64}$Cu (39). Radiolabeling these peptides with $^{18}$F better matches radioisotope kinetics (1.8 h half-time) with the rapid uptake in tumor and clearance from background (effective imaging at 1 h post-injection), which is critical for clinical translation. The peptides were effectively labeled site-specifically at the N-terminal amine with $^{18}$F using SFB and retain high stability and activity. The tracers specifically target tumor (5.0±1.8 and 4.7±1.8 tumor:muscle and 6.0±1.1 and 3.1±0.8 tumor:blood for $^{18}$F-FB-R$_0$1 and $^{18}$F-FB-S$_0$2, respectively) in an integrin $\alpha_v\beta_6$-specific manner (statistically significantly reduced uptake in target-negative 293 xenografts).

In addition to improved positron yield and reduced dosimetry relative to $^{64}$Cu, the $^{18}$F versions of these peptides have greatly reduced liver and kidney retention. R$_0$1 exhibits a five-fold reduction in renal signal (in % ID/g) from 80±16 for $^{64}$Cu-DOTA to 16±4 for $^{18}$F-FB at 1 h. S$_0$2 decreases four-fold from 29±10 to 7±3. Hepatic signal (in % ID/g) decreases from 3.1±0.6 to 1.2±0.2 for R$_0$1 and 4.4±1.2 to 0.3±0.1 for S$_0$2. This renal reduction is in agreement with previously observed results for several affibody domains. Affibody Z$_{HER2:477}$ kidney uptake (in % ID/g) was reduced from 206±22 to 19±1 for the monomer and 114±11 to 7±1 for the dimer when labeling was changed from $^{64}$Cu-DOTA(16) to $^{18}$F-N-(4-fluorobenzylidene)oxime (42). Similarly, affibody Z$_{HER2-342}$ kidney uptake (in % ID/g) decreased from 172±13 at 4 h with $^{111}$In-DOTA (43) to 10±3 at 2 h with N-2-(4-$^{18}$F-fluorobenzamido)ethylmaleimide (44).

Tumor uptake is also reduced in the $^{18}$F-labeled peptides relative to the $^{64}$Cu-labeled peptides, although to a lesser extent than the beneficial kidney and liver reductions. R$_0$1 tumor signal (in % ID/g) decreases from 4.7±0.9 at 1 h to 2.3±0.6 and 1.9±0.5 at 0.5 h and 1 h, respectively. S$_0$2 decreases from 2.1±0.5 at 1 h to 1.3±0.4 h and 0.7±0.3 at 0.5 and 1 h, respectively. As noted above, molecular specificity remains high in relation to muscle, blood, and integrin $\alpha_v\beta_6$-negative tumors.

Thus, $^{18}$F-FB-R$_0$1 is a prime candidate for clinical translation. Though only semi-quantitative comparisons can be made because of the use of different animal models, $^{18}$F-FB-R$_0$1 compares favorably to alternative integrin $\alpha_v\beta_6$ tracers. This probe has greater tumor uptake (2.3±0.6 and 1.9±0.5 at 0.5 h and 1 h for $^{18}$F-FB-R$_0$1 vs. 0.7±0.2 for $^{18}$F-FB-A20FMDV2 at 1 h), tumor:muscle contrast (5.0±1.8 vs. 1.3), and tumor:blood contrast (6.0±1.1 vs. 3.3) than $^{18}$F-A20FMDV2, albeit with higher renal signal (27±4 and 16±4 at 0.5 h and 1 h vs. 3.3±0.8). Addition of polyethylene glycol to the A20FMDV2 peptide (45) increased the tumor (1.9±0.4) and kidney (19±5) to uptake values essentially equal to those observed for $^{18}$F-FB-R$_0$1. Importantly, $^{18}$F-FB-R$_0$1 is 87% stable in human serum at 2 h whereas urine analysis at 1 h post-injection reveals three metabolites and no intact tracer for $^{18}$F-A20 and one major metabolite for $^{18}$F-PEG-A20FMDV2 (though data was not shown). Increased stability may reduce off-target effects from metabolites including reduced immunogenicity, which is now under study.

A clinical molecular imaging agent for integrin $\alpha_v\beta_6$ could have broad impact as increased expression is observed on multiple cancers (1-9). In particular, there is a critical need for a molecular imaging agent for early detection of pancreatic cancer as 40-45% of pancreatic cancers present with metastasis and 40% present with local advancement (40). Moreover, a molecular imaging agent could be used for patient treatment stratification and therapy monitoring. Integrin $\alpha_v\beta_6$ expression is undetectable in healthy pancreas but has elevated expression in pancreatic ductal adenocarcinoma (46). It is noteworthy that the PET tracers in the current work exhibit low uptake in healthy pancreas (0.3±0.1% for $^{18}$F-FB-R$_0$1 and 0.03±0.01% for $^{18}$F-FB-S$_0$2), which is imperative for clinical translation towards this application.

Example 7

Figure 8:
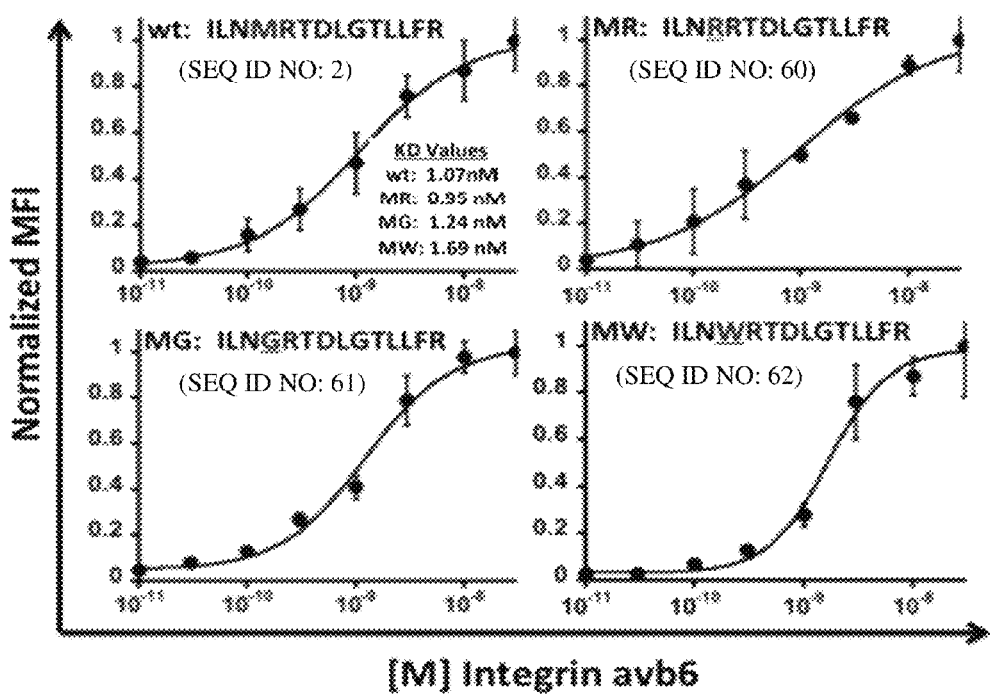
FIG. 8 is a series of graphs showing the $K_D$ values resulting from site directed evolution of $\alpha_v\beta_6$ cystine knot 100 pM sort products wild-type (wt), arginine substitution (MΔR), glycine substitution (MΔG), and tryptophan substitution (MΔW).

Substituted Ro1 $\alpha_v\beta_6$ Cystine Knot Peptides (FIG. 8)

During protein folding studies, it was found that the methionine residue located within Loop-1 of the R$_0$1 peptide scaffold (preceding the binding motif RTDL-L) was being oxidized. This oxidation negatively affects protein stability. In order to avoid these issues during the folding process, it has now been found that different amino acids can be substituted for the methionine residue underlined below. These may be synthesized as described above.

Using the R$_0$1 peptide scaffold (from peptide MoCoTI-II, as described above), the methionine residue (M below) was substituted with glycine, arginine, and tryptophan residues using site directed evolution. The new R$_0$1 substituted Loop-1 peptide sequences are presented below:

| | | |
|---|---|---|
| Wild-type: | ILN<u>M</u>RTDLGTLLFR | (SEQ ID NO: 2) |
| MΔR: | ILN<u>R</u>RTDLGTLLFR | (SEQ ID NO: 60) |
| MΔG: | ILN<u>G</u>RTDLGTLLFR | (SEQ ID NO: 61) |
| MΔW: | ILN<u>W</u>RTDLGTLLFR | (SEQ ID NO: 62) |

It should be understood that the above sequences are loop portions of the full length sequence R$_0$1 (SEQ ID NO: 2). That is, in SEQ ID NO: 8, in the above sequences are represented by X$_4$ being, respectively R, G, or W. More explicitly, X1 is I; X2 is L; X3 is N; X4 is M; X5 is G; X6 is T; X7 is L; X8 is F; X9 is R; X10 is R; X11 is P; X12 is G; X13 is A; X14 is R; X15 is G; and X16 is Y.

The new substituted R$_0$1 scaffolds were tested for their ability to bind integrin avb6 in cell sorting studies, showing binding of these peptides as expressed on the surface of yeast. The K$_D$ of MΔR, MΔG, and MΔW were measured to be 0.95 nM, 1.24 nM, and 1.69 nM, respectively. The MΔR and MΔG peptides were found to be closest to (and essentially equivalent to) the wild type R$_0$1 peptide, which had a K$_D$ value of 1.07 nM.

Example 8

Figure 9A:
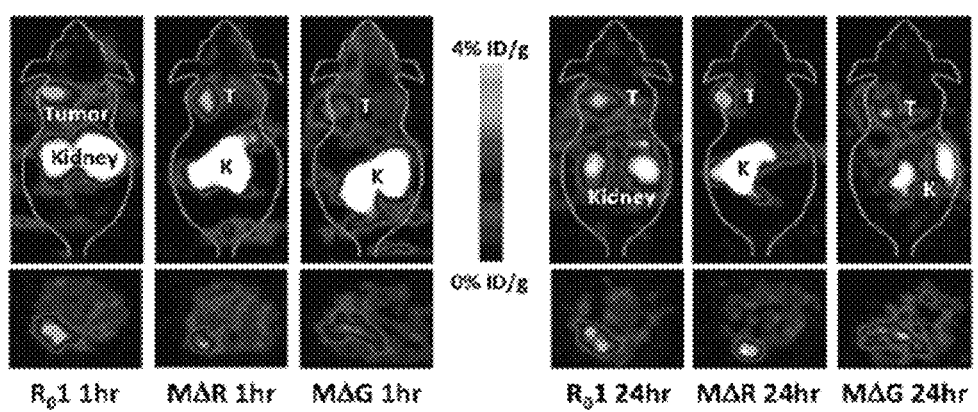
FIG. 9A is a series of microPET photographic images of $^{64}$Cu-DOTA $R_o1$ wild-type (M-M), MΔR, and MΔG peptides.
Figure 9B:
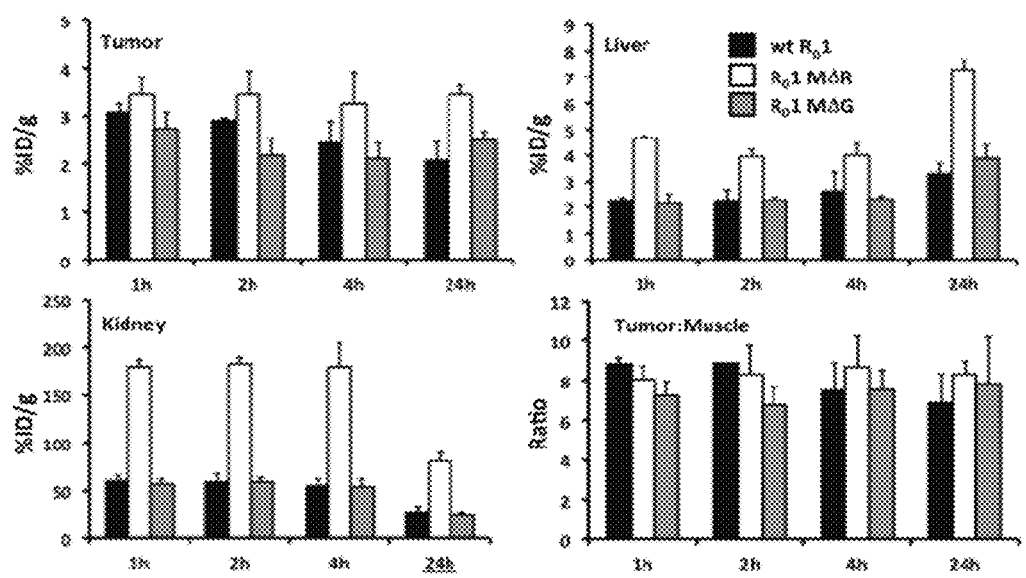
FIG. 9B is a series of graphs showing the quantification of the microPET images of FIG. 9A.

$^{64}$Cu-Labeled Ro1 wt, MΔR, and MΔG for microPET Imaging of Integrin $\alpha_v\beta_6$ Tumors (FIGS. 9A and 9B)

Tissue uptake of the M-substituted peptides MΔR and MΔG was determined by injecting mice with $^{64}$Cu-DOTA-R$_0$1 "wild-type" and $^{64}$Cu-DOTA labeled MΔR and MΔG peptides. Measurements were made over 24 hours. $^{64}$Cu-DOTA-wild-type, MΔR and MΔG appeared to be taken up by and excreted by the kidneys and they also resulted in similar tumor-to-muscle ratios between 7-9 at 1 h, 2 h, 4 h, and 24 h post injection. $^{64}$Cu-DOTA-MΔG had comparable results the wild-type R$_0$1 peptide in the tumor, liver, and kidney). $^{64}$Cu-DOTA-MΔR resulted in higher uptake in the tumor and liver and considerably higher uptake in the kidney compared to the wild-type.

Example 9

Figure 10:
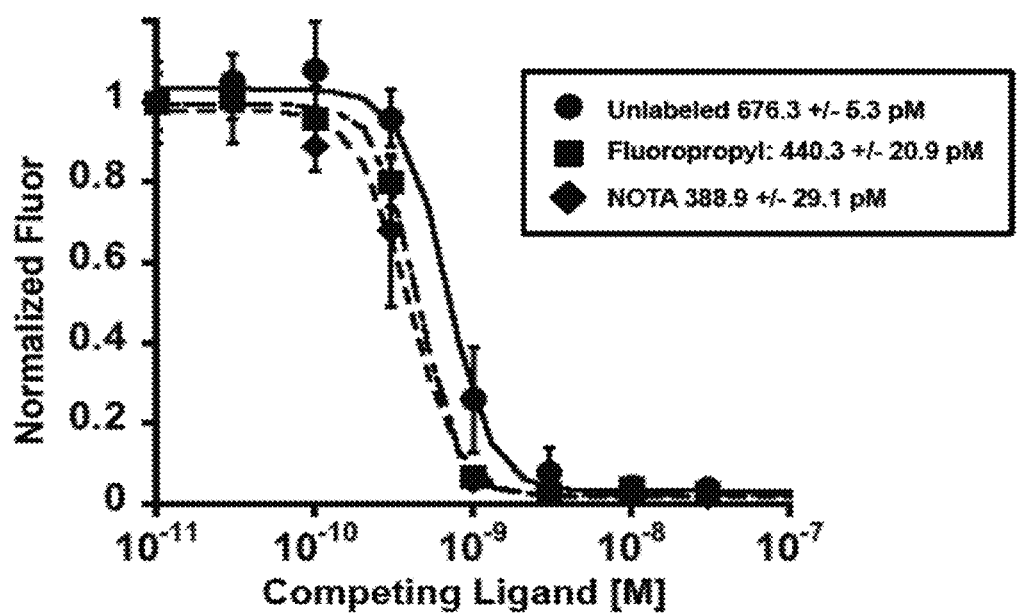
FIG. 10 is a graph showing that N-terminus fluoropropyl and NOTA labeling does not adversely affect binding affinity.

Binding Activity of NOTA and Fluoropropyl Based Labeling (FIG. 10)

To determine whether the chelator used to attach the PET label affects the pharmacokinetics of the peptides, the binding affinity of chelator 1,4,7-triazacyclononanetriacetic acid (NOTA) and label fluoropropyl were tested in a competitive binding experiment. To determine whether the chelator used to attach the PET label affects the pharmacokinetics of the peptides, the binding affinity of 1,4,7-triazacyclononanetri-acetic acid (NOTA) and fluoropropyl were tested in a competitive binding experiment with the A11 labeling was done at the N-terminus of the peptide after folding. Results showed that NOTA and fluoropropyl had slightly lower specific binding affinities compared to the unlabeled peptide. The results indicate that neither chelator adversely affects binding affinity of the peptide to the target alpha-V beta 6 integrin. Further studies (data not shown) have demonstrated that 18F fluoropropyl radiolabelling can be carried out with high specificity on the subject peptides, in particular MΔG. 18F is a positron emitter useful in PET imaging.

Example 10

Figure 11:
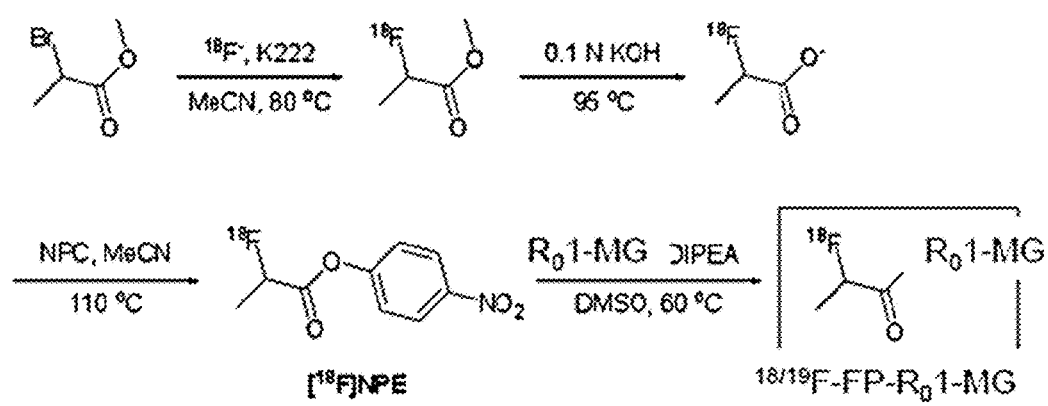
FIG. 11 is a schematic representation of the coupling of $F^{18/19}$ to a peptide, namely Ro1, MΔG.

$^{19}$F-FP-R$_0$1-MG Synthesis and Characterization
(FIG. 11)

2-Fluoropropionic (FP) acid was esterified using either N,N,N',N'-Tetramethyl-O-(N-succinimidyl)uranium tetrafluoroborate (TSTU) to produce the succinimide ester, or Bis(4-nitrophenyl)carbonate to produce the nitrophenyl ester. Active ester compounds were coupled to the sole N-terminus amine of R01-MG to yield 19F-FP-R01-MG. The reaction with either ester yielded a 50:50 mixture of products with correct mass. Moreover, their binding affinities for integrin avb6 were approximately equal suggesting that they are structural isomers of the same compound. 1D-NMR of the nitrophenyl ester precursor indicated a racemic mixture around the fluorinated chiral center. However, isocratic HPLC analysis of the starting peptide material indicated multiple species, which would appear as a single peak on a typical HPLC gradient. The final product(s) can be spaced to elute a full minute apart from each other with an isocratic HPLC method. They were purified to homogeneity as separate compounds with identical biochemical and biophysical properties with the exception of the apparent difference in hydrophobicity between the two products.

conclusion

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

References

1. Hynes R O. Integrins: bidirectional, allosteric signaling machines. Cell 2002; 110: 673-87.
2. Bandyopadhyay A, Raghavan S. Defining the role of integrin alphavbeta6 in cancer. Curr Drug Targets 2009; 10: 645-52.
3. Drake C J, Cheresh D A, Little C D. An antagonist of integrin alpha v beta 3 prevents maturation of blood vessels during embryonic neovascularization. J Cell Sci 1995; 108 (Pt 7): 2655-61.
4. Varner J A, Brooks P C, Cheresh D A. REVIEW: the integrin alpha V beta 3: angiogenesis and apoptosis. Cell Adhes Commun 1995; 3: 367-74.
5. Ahmed N, Pansino F, Clyde R, Murthi P, Quinn M A, Rice G E, et al. Overexpression of alpha(v)beta6 integrin in serous epithelial ovarian cancer regulates extracellular matrix degradation via the plasminogen activation cascade. Carcinogenesis 2002; 23: 237-44.
6. Sipos B, Hahn D, Carceller A, Piulats J, Hedderich J, Kalthoff H, et al. Immunohistochemical screening for beta6-integrin subunit expression in adenocarcinomas using a novel monoclonal antibody reveals strong up-regulation in pancreatic ductal adenocarcinomas in vivo and in vitro. Histopathology 2004; 45: 226-36.
7. Hausner S H, DiCara D, Marik J, Marshall J F, Sutcliffe J L. Use of a peptide derived from foot-and-mouth disease virus for the noninvasive imaging of human cancer: generation and evaluation of 4-[18F]fluorobenzoyl A20FMDV2 for in vivo imaging of integrin alphavbeta6 expression with positron emission tomography. Cancer Res 2007; 67: 7833-40.
8. Hausner S H, Abbey C K, Bold R J, Gagnon M K, Marik J, Marshall J F, et al. Targeted in vivo imaging of integrin alphavbeta6 with an improved radiotracer and its relevance in a pancreatic tumor model. Cancer Res 2009; 69: 5843-50.
9. Hausner S H, Kukis D L, Gagnon M K, Stanecki C E, Ferdani R, Marshall J F, et al. Evaluation of [64Cu]Cu-DOTA and [64Cu]Cu-CB-TE2A chelates for targeted positron emission tomography with an alphavbeta6-specific peptide. Mol Imaging 2009; 8: 111-21.
10. Hazelbag S, Kenter G G, Gorter A, Dreef E J, Koopman L A, Violette S M, et al. Overexpression of the alpha v beta 6 integrin in cervical squamous cell carcinoma is a prognostic factor for decreased survival. J Pathol 2007; 212: 316-24.
11. Bates R C, Bellovin D I, Brown C, Maynard E, Wu B, Kawakatsu H, et al. Transcriptional activation of integrin beta6 during the epithelial-mesenchymal transition defines a novel prognostic indicator of aggressive colon carcinoma. J Clin Invest 2005; 115: 339-47.
12. Elayadi A N, Samli K N, Prudkin L, Liu Y H, Bian A, Xie X J, et al. A peptide selected by biopanning identifies the integrin alphavbeta6 as a prognostic biomarker for nonsmall cell lung cancer. Cancer Res 2007; 67: 5889-95.
13. Bittle J L, Houghten R A, Alexander H, Shinnick T M, Sutcliffe J G, Lerner R A, et al. Protection against foot-and-mouth disease by immunization with a chemically synthesized peptide predicted from the viral nucleotide sequence. Nature 1982; 298: 30-3.
14. Kraft S, Diefenbach B, Mehta R, Jonczyk A, Luckenbach G A, Goodman S L. Definition of an unexpected ligand recognition motif for alphav beta6 integrin. J Biol Chem 1999; 274: 1979-85.
15. Hsiao J R, Chang Y, Chen Y L, Hsieh S H, Hsu K F, Wand C F, et al. Cyclic alphavbeta6-targeting peptide selected from biopanning with clinical potential for head and neck squamous cell carcinoma. Head Neck 2010; 32: 160-72.
16. Nothelfer E M, Zitzmann-Kolbe S, Garcia-Boy R, Kramer S, Herold-Mende C, Altmann A, et al. Identification and characterization of a peptide with affinity to head and neck cancer. J Nucl Med 2009; 50: 426-34.
17. Gagnon M K, Hausner S H, Marik J, Abbey C K, Marshall J F, Sutcliffe J L. High-throughput in vivo screening of targeted molecular imaging agents. Proc Natl Acad Sci USA 2009; 106: 17904-9.
18. Tangri S, LiCalsi C, Sidney J, Sette A. Rationally engineered proteins or antibodies with absent or reduced immunogenicity. Curr Med Chem 2002; 9: 2191-9.

19. Kimura R H, Cheng Z, Gambhir S S, Cochran J R. Engineered knottin peptides: a new class of agents for imaging integrin expression in living subjects. Cancer Res 2009; 69: 2435-42.
20. Miao Z, Ren G, Liu H, Kimura R H, Jiang L, Cochran J R, et al. An engineered knottin peptide labeled with 18F for PET imaging of integrin expression. Bioconjug Chem 2009; 20: 2342-7.
21. Willmann J K, Kimura R H, Deshpande N, Lutz A M, Cochran J R, Gambhir S S. Targeted contrast-enhanced ultrasound imaging of tumor angiogenesis with contrast microbubbles conjugated to integrin-binding knottin peptides. J Nucl Med; 51: 433-40.
22. Kimura R H, Levin A M, Cochran F V, Cochran J R. Engineered cystine knot peptides that bind alphavbeta3, alphavbeta5, and alpha5beta1 integrins with low-nanomolar affinity. Proteins 2009; 77: 359-69.
23. Colgrave M L, Craik D J. Thermal, chemical, and enzymatic stability of the cyclotide kalata B1: the importance of the cyclic cystine knot. Biochemistry 2004; 43: 5965-75.
24. Gran L. Oxytocic principles of *Oldenlandia affinis*. Lloydia 1973; 36: 174-8.
25. Gran L, Sletten K, Skjeldal L. Cyclic peptides from *Oldenlandia affinis* DC. Molecular and biological properties. Chem Biodivers 2008; 5: 2014-22.
26. Swers J S, Kellogg B A, Wittrup K D. Shuffled antibody libraries created by in vivo homologous recombination and yeast surface display. Nucleic Acids Res 2004; 32: e36.
27. Lipovsek D, Lippow S M, Hackel B J, Gregson M W, Cheng P, Kapila A, et al. Evolution of an interloop disulfide bond in high-affinity antibody mimics based on fibronectin type III domain and selected by yeast surface display: molecular convergence with single-domain camelid and shark antibodies. J Mol Biol 2007; 368: 1024-41.
28. Wu Y, Zhang X, Xiong Z, Cheng Z, Fisher D R, Liu S, et al. microPET imaging of glioma integrin {alpha}v{beta}3 expression using (64)Cu-labeled tetrameric RGD peptide. J Nucl Med 2005; 46: 1707-18.
29. Jiang L, Kimura R H, Miao Z, Silverman A P, Ren G, Liu H, et al. Evaluation of a (64)Cu-labeled cystine-knot peptide based on agouti-related protein for PET of tumors expressing alphavbeta3 integrin. J Nucl Med; 51: 251-8.
30. Heitz A, Hernandez J F, Gagnon J, Hong T T, Pham T T, Nguyen T M, et al. Solution structure of the squash trypsin inhibitor MCoTI-II. A new family for cyclic knottins. Biochemistry 2001; 40: 7973-83.
31. Cemazar M, Joshi A, Daly N L, Mark A E, Craik D J. The structure of a two-disulfide intermediate assists in elucidating the oxidative folding pathway of a cyclic cystine knot protein. Structure 2008; 16: 842-51.
32. Wu G, Morris S M, Jr. Arginine metabolism: nitric oxide and beyond. Biochem J 1998; 336 (Pt 1): 1-17.
33. Tolmachev V, Velikyan I, Sandstrom M, Orlova A. A HER2-binding Affibody molecule labelled with 68Ga for PET imaging: direct in vivo comparison with the 111In-labelled analogue. Eur J Nucl Med Mol Imaging; 37: 1356-67.
34. Miao Z, Ren G, Liu H, Jiang L, Cheng Z. Small-animal PET imaging of human epidermal growth factor receptor positive tumor with a 64Cu labeled affibody protein. Bioconjug Chem; 21: 947-54.
35. Tolmachev V, Rosik D, Wallberg H, Sjoberg A, Sandstrom M, Hansson M, et al. Imaging of EGFR expression in murine xenografts using site-specifically labelled anti-EGFR 111In-DOTA-Z EGFR:2377 Affibody molecule: aspect of the injected tracer amount. Eur J Nucl Med Mol Imaging; 37: 613-22.
36. Hansson M, Ringdahl J, Robert A, Power U, Goetsch L, Nguyen T N, et al. An in vitro selected binding protein (affibody) shows conformation-dependent recognition of the respiratory syncytial virus (RSV) G protein. Immunotechnology 1999; 4: 237-52.
37. Friedman M, Nordberg E, Hoiden-Guthenberg I, Brismar H, Adams G P, Milsson F Y, et al. Phage display selection of Affibody molecules with specific binding to the extracellular domain of the epidermal growth factor receptor. Protein Eng Des Sel 2007; 20: 189-99.
38. Hogbom M, Eklund M, Nygren P A, Nordlund P. Structural basis for recognition by an in vitro evolved affibody. Proc Natl Acad Sci USA 2003; 100: 3191-6.
39. Kimura R H, Teed R, Hackel B J, Chuang C Z, Sathirachinda A, Gambhir S S. submitted.
40. Nieto J, Grossbard M L, Kozuch P. Metastatic Pancreatic Cancer 2008: Is the Glass Less Empty? *The Oncologist* 2008; 13: 562-76.
41. Loening A M, Gambhir S S. AMIDE: a free software tool for multimodality medical image analysis. *Mol Imaging* 2003; 2: 131-7.
42. Cheng Z, De Jesus O P, Namavari M, et al. Small-animal PET imaging of human epidermal growth factor receptor type 2 expression with site-specific 18F-labeled protein scaffold molecules. *J Nucl Med* 2008; 49: 804-13.
43. Ahlgren S, Orlova A, Rosik D, et al. Evaluation of maleimide derivative of DOTA for site-specific labeling of recombinant affibody molecules. *Bioconjug Chem* 2008; 19: 235-43.
44. Kramer-Marek G, Kiesewetter D O, Capala J. Changes in HER2 Expression in Breast Cancer Xenografts After Therapy Can Be Quantified Using PET and 18F-Labeled Affibody Molecules. *J Nucl Med* 2009; 50: 1131-9.
45. Hausner S H, Abbey C K, Bold R J, et al. Targeted in vivo imaging of integrin alphavbeta6 with an improved radiotracer and its relevance in a pancreatic tumor model. *Cancer Research* 2009; 69: 5843-50.
46. Sipos B, Hahn D, Carceller A, et al. Immunohistochemical screening for beta6-integrin subunit expression in adenocarcinomas using a novel monoclonal antibody reveals strong up-regulation in pancreatic ductal adenocarcinomas in vivo and in vitro. *Histopathology* 2004; 45: 226-36.

What is claimed is:

1. A peptide having specific binding to alpha-v-beta-6 integrin, comprising a binding portion between two cysteine residues and a scaffold portion, said peptide being at least 83% identical to a sequence selected from the group consisting of:
(a) GCILNMRTDLGTLLFRCRRDSDCPGACICRGNGYCG (SEQ ID NO: 2),
(b) GCRSLARTDLDHLRGRCRRDSDCPGACICRGNGYCG (SEQ ID NO: 3),
(c) GCRSLARTDLDHLRGRCEEDSDCLAECICEENGFCG (SEQ ID NO: 4),
(d) GCRSLARTDLDHLRDRCSSDSDCLAECICLENGFCG (SEQ ID NO: 5),
(e) GCILNRRTDLGTLLFRCRRDSDCPGACICRGNGYCG (SEQ ID NO: 63),
(f) GCILNGRTDLGTLLFRCRRDSDCPGACICRGNGYCG (SEQ ID NO: 64), and
(g) GCILNWRTDLGTLLFRCRRDSDCPGACICRGNGYCG (SEQ ID NO: 65).

2. The peptide of claim 1 wherein the peptide is at least 88% (32/36 amino acids) or at least 94% (34/36 amino acids) identical to one of the peptides listed in (a) through (g).

3. A peptide having a sequence with a formula of (SEQ ID NO: 8)
GCX$_1$ X$_2$ X$_3$ X$_4$ RTDLX$_5$ X$_6$ LX$_7$ X$_8$ RCX$_9$ X$_{10}$ DSDCX$_{11}$ X$_{12}$ X$_{13}$ CICX$_{14}$ X$_{15}$ NG X$_{16}$ CG, wherein, X$_1$ is I or R; X$_2$ is L or S; X$_3$ is N or L; X$_4$ is M, A, R, G, or W; X$_5$ is G or D; X$_6$ is T or H; X$_7$ is L or R; X$_8$ is F, D or G; X$_9$ is R, E or S; X$_{10}$ is R, S, or E; X$_{11}$ is P or L; X$_{12}$ is G or A; X$_{13}$ is A or E; X$_{14}$ is R, E or L; X$_{15}$ is G or E; and X$_{16}$ is Y or F.

4. The peptide of claim 3 in a pharmacologically acceptable excipient or carrier.

5. The peptide of claim 4 further comprising a radiolabel attached to said peptide.

6. The peptide of claim 3 having a chelator linked to an amino acid of said peptide.

7. The peptide of claim 6, wherein said chelator is 1,4,7-triazacyclononanetriacetic acid (NOTA).

8. The peptide of claim 7, wherein said chelator is bound to a label.

9. The peptide of claim 8, wherein said label is a radiolabel.

10. The peptide of claim 9, wherein said label is a halogen or a metal.

11. The peptide of claim 10, wherein said label is $^{64}$Cu or $^{18}$F.

12. A method of detecting an alpha-v-beta-6 integrin comprising:
(a) contacting the alpha-v-beta-6 integrin with a labeled peptide having a sequence at least 83% identical to one of
GCILNMRTDLGTLLFRCRRDSDCPGACICRGNGYCG (SEQ ID NO: 2),
GCRSLARTDLDHLRGRCRRDSDCPGACICRGNGYCG (SEQ ID NO: 3),
GCRSLARTDLDHLRGRCEEDSDCLAECICEENGFCG (SEQ ID NO: 4),
GCRSLARTDLDHLRDRCSSDSDCLAECICLENGFCG (SEQ ID NO: 5),
GCILNRRTDLGTLLFRCRRDSDCPGACICRGNGYCG (SEQ ID NO: 63),
GCILNGRTDLGTLLFRCRRDSDCPGACICRGNGYCG (SEQ ID NO: 64), or
GCILNWRTDLGTLLFRCRRDSDCPGACICRGNGYCG (SEQ ID NO: 65); and
(b) detecting binding of the labeled peptide to the alpha-v-beta-6 integrin by means of the label.

13. The method of claim 12, wherein said alpha-v-beta-6 integrin is expressed on a cancer cell contacted by said labeled peptide.

14. The method of claim 13, wherein said cancer cell is in a tumor ex vivo.

15. The method of claim 13, wherein said cancer cell is detected in a living mammal and further comprising a step of imaging tissue containing said cancer cell.

16. The method of claim 12, wherein said peptide carries a positron emission tomography (PET) imaging label.

17. The method of claim 12, wherein said peptide is conjugated to a radiolabel or a toxin.

18. The method of claim 12 wherein said labeled peptide is contained in a pharmacologically acceptable excipient or carrier and is delivered intravenously to a subject having tissue expressing alpha-v-beta-6 integrin.

19. A method of treating viral infection in a nonhuman animal at risk for infection with a virus that binds alpha-v-beta-6 integrin, comprising administering to said animal a peptide having a sequence (SEQ ID NO: 8)
GCX$_1$ X$_2$ X$_3$ X$_4$ RTDLX$_5$ X$_6$ LX$_7$ X$_8$ RCX$_9$ X$_{10}$ DSDCX$_{11}$ X$_{12}$ X$_{13}$ CICX$_{14}$ X$_{15}$ NG X$_{16}$ CG, wherein, X$_1$ is I or R; X$_2$ is L or S; X$_3$ is N or L; X$_4$ is M, A, R, G, or W; X$_5$ is G or D; X$_6$ is T or H; X$_7$ is L or R; X$_8$ is F, D or G; X$_9$ is R, E or S; X$_{10}$ is R, S, or E; X$_{11}$ is P or L; X$_{12}$ is G or A; X$_{13}$ is A or E; X$_{14}$ is R, E or L; X$_{15}$ is G or E; and X$_{16}$ is Y or F.

20. The method of claim 19, wherein said animal is a cloven hoof animal and said virus is foot-and-mouth disease virus.

21. A method of delivering an agent to a cancer cell expressing alpha-v-beta-6 integrin, comprising contacting said cell with a peptide having a sequence (SEQ ID NO: 8)
GCX$_1$ X$_2$ X$_3$ X$_4$ RTDLX$_5$ X$_6$ LX$_7$ X$_8$ RCX$_9$ X$_{10}$ DSDCX$_{11}$ X$_{12}$ X$_{13}$ CICX$_{14}$ X$_{15}$ NG X$_{16}$ CG, wherein, $X_1$ is I or R; $X_2$ is L or S; $X_3$ is N or L; $X_4$ is M, A, R, G, or W; $X_5$ is G or D; $X_6$ is T or H; $X_7$ is L or R; $X_8$ is F, D or G; $X_9$ is R, E or S; $X_{10}$ is R, S, or E; $X_{11}$ is P or L; $X_{12}$ is G or A; $X_{13}$ is A or E; $X_{14}$ is R, E or L; $X_{15}$ is G or E; and $X_{16}$ is Y or F, and said peptide is linked to said agent.

22. The method of claim 21 wherein said agent is selected from the group consisting of a peptide toxin and a radionuclide.

* * * * *